(12) United States Patent
McGonigle et al.

(10) Patent No.: US 8,478,538 B2
(45) Date of Patent: Jul. 2, 2013

(54) SELECTION OF SIGNAL REGIONS FOR PARAMETER EXTRACTION

(75) Inventors: Scott McGonigle, Edinburgh (GB); Paul S. Addison, Edinburgh (GB); James N. Watson, Dunfermline (GB)

(73) Assignee: Nellcor Puritan Bennett Ireland, Galway (IE)

( * ) Notice: Subject to any disclaimer, the term of this patent is extended or adjusted under 35 U.S.C. 154(b) by 990 days.

(21) Appl. No.: 12/437,329

(22) Filed: May 7, 2009

(65) Prior Publication Data

US 2010/0286495 A1 Nov. 11, 2010

(51) Int. Cl.
*G06F 7/00* (2006.01)

(52) U.S. Cl.
USPC ............. 702/19; 702/20; 703/11; 707/700; 600/1

(58) Field of Classification Search
USPC ...................................... 702/19–20
See application file for complete search history.

(56) References Cited

U.S. PATENT DOCUMENTS

| | | | |
|---|---|---|---|
| 4,800,495 A | 1/1989 | Smith | |
| 5,218,962 A | 6/1993 | Mannheimer et al. | |
| 5,482,036 A | 1/1996 | Diab et al. | |
| 5,490,505 A | 2/1996 | Diab et al. | |
| 5,517,988 A | 5/1996 | Gerhard | |
| 5,558,096 A | 9/1996 | Palatnik | |
| 5,632,272 A | 5/1997 | Diab et al. | |
| 5,662,106 A | 9/1997 | Swedlow et al. | |
| 5,685,299 A | 11/1997 | Diab et al. | |
| 5,713,355 A | 2/1998 | Richardson et al. | |
| 5,769,785 A | 6/1998 | Diab et al. | |
| 5,820,550 A | 10/1998 | Polson | |
| 6,002,952 A | 12/1999 | Diab et al. | |
| 6,036,642 A | 3/2000 | Diab et al. | |
| 6,067,462 A | 5/2000 | Diab et al. | |
| 6,081,735 A | 6/2000 | Diab et al. | |
| 6,206,830 B1 | 3/2001 | Diab et al. | |
| 6,263,222 B1 | 7/2001 | Diab et al. | |
| 6,501,975 B2 | 12/2002 | Diab et al. | |
| 6,519,486 B1 | 2/2003 | Edgar, Jr. et al. | |
| 6,631,281 B1 | 10/2003 | Kästle | |
| 6,654,623 B1 | 11/2003 | Kästle | |
| 6,654,624 B2 | 11/2003 | Diab et al. | |
| 6,684,090 B2 | 1/2004 | Ali et al. | |
| RE38,476 E | 3/2004 | Diab et al. | |
| 6,699,194 B1 | 3/2004 | Diab et al. | |
| RE38,492 E | 4/2004 | Diab et al. | |
| 6,805,673 B2 | 10/2004 | Dekker | |
| 6,810,277 B2 | 10/2004 | Edgar, Jr. et al. | |
| 6,811,538 B2 | 11/2004 | Westbrook et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,839,659 B2 | 1/2005 | Tarassenko et al. | |
| 6,852,083 B2 | 2/2005 | Caro et al. | |
| 6,996,427 B2 | 2/2006 | Ali et al. | |
| 7,006,856 B2 | 2/2006 | Baker, Jr. et al. | |
| 7,020,507 B2 | 3/2006 | Scharf et al. | |
| 7,072,702 B2 | 7/2006 | Edgar, Jr. et al. | |
| 7,139,599 B2 | 11/2006 | Terry | |
| 7,162,288 B2 | 1/2007 | Nordstrom et al. | |
| 7,248,910 B2 | 7/2007 | Li et al. | |
| 7,355,512 B1 | 4/2008 | Al-Ali | |
| 7,367,339 B2 | 5/2008 | Hickle | |
| 7,381,188 B1 | 6/2008 | Farazi | |
| 7,407,485 B2 | 8/2008 | Huiku | |
| 7,460,899 B2 | 12/2008 | Almen | |
| 7,499,740 B2 | 3/2009 | Nordstrom et al. | |
| 7,582,061 B2 | 9/2009 | Li et al. | |
| 2003/0212336 A1 | 11/2003 | Lee et al. | |
| 2004/0242979 A1 | 12/2004 | Kawasaki | |
| 2005/0004479 A1 | 1/2005 | Townsend et al. | |
| 2005/0070774 A1 | 3/2005 | Addison et al. | |
| 2005/0165316 A1 | 7/2005 | Lowery et al. | |
| 2005/0197579 A1 | 9/2005 | Baker, Jr. | |
| 2006/0135860 A1 | 6/2006 | Baker, Jr. et al. | |
| 2006/0137577 A1 | 6/2006 | Chang et al. | |
| 2006/0195025 A1 | 8/2006 | Ali et al. | |
| 2006/0241708 A1 | 10/2006 | Boute | |
| 2006/0258927 A1 | 11/2006 | Edgar, Jr. et al. | |
| 2007/0238937 A1 | 10/2007 | Chang et al. | |
| 2008/0262326 A1 | 10/2008 | Hete et al. | |

FOREIGN PATENT DOCUMENTS

| | | |
|---|---|---|
| WO | WO 00/21438 | 4/2000 |
| WO | 2009016334 A1 | 2/2009 |
| WO | 2010001246 A2 | 1/2010 |
| WO | 2010001249 A1 | 1/2010 |

OTHER PUBLICATIONS

PCT International Search Report, Applicant's Reference PE953786WO, International Application No. PCT/GB2010/000839, International Filing Date: Apr. 26, 2010, Priority Date: Jul. 5, 2009, Applicant: Nellcor Puritan Bennett Ireland.

Addison, Paul S., The Illustrated Wavelet Transform Handbook, Taylor & Francis Group, 2002.

*Primary Examiner* — Mary Zeman

(57) ABSTRACT

According to embodiments, techniques for extracting a signal parameter from a selected region of a generally repetitive signal are disclosed. A pulse oximetry system including a sensor or probe may be used to obtain an original photoplethysmograph (PPG) signal from a subject. A filter transformation may be applied to the original PPG signal to produce a baseline PPG signal. The baseline PPG signal may contain artifacts and/or noise, and a region of the baseline PPG signal suitable for extracting the signal parameter may be selected. A suitable region of the baseline PPG signal may be selected by applying one or more thresholds to the baseline PPG signal, where the values of the thresholds may be set based on derivative values, amplitude-based percentiles, and/or local minima and maxima of the baseline PPG signal. A portion of the original PPG signal corresponding to the selected region may be processed, and the signal parameter may be extracted from the processed region. In an embodiment, the signal parameter may correspond to the respiration rate of a patient.

20 Claims, 16 Drawing Sheets

SELECTION OF SIGNAL REGIONS FOR PARAMETER EXTRACTION

SUMMARY

The present disclosure is related to signal processing systems and methods, and more particularly, to systems and methods for extracting a signal parameter from a selected region of a generally repetitive signal, and/or a biological signal, such as a photoplethysmograph (PPG) signal.

In an embodiment, a technique for extracting a signal parameter from a PPG signal is disclosed. An original PPG signal may be obtained from a sensor, and the original PPG signal may be stored in a first computer memory location. A baseline PPG signal may be produced by applying a filter transformation to the original PPG signal, where the filter transformation may partially or fully remove a pulse component from the original PPG signal. The baseline PPG signal may be stored in a second computer memory location. One or more regions of the baseline PPG signal may be identified by applying one or more thresholds to the baseline PPG signal, where the values of the one or more thresholds depend on a set of signal amplitude values of the baseline PPG signal. A region from the one or more identified regions may be selected, and a portion of the original PPG signal corresponding to the selected region may be processed to remove artifacts from the portion of the original PPG signal. The signal parameter may then be extracted from the processed portion of the original PPG signal.

In an embodiment, suitable regions of the baseline PPG signal may be identified by computing a set of derivative values of the baseline PPG signal, and setting an upper threshold value and a lower threshold value based on the set of derivative values. Regions of the baseline PPG signal having signal amplitude values located within the lower threshold value and the upper threshold value may be selected.

In an embodiment, regions of the baseline PPG signal may be identified by computing a set of amplitude-based percentiles of the baseline PPG signal, and by setting upper and lower threshold values based on the computed set of amplitude-based percentiles. Regions of the baseline PPG signal suitable for parameter extraction may be identified by identifying regions for which signal amplitude values of the baseline PPG signal are located within the lower threshold value and the upper threshold value.

In an embodiment, regions of the baseline PPG signal may be identified by computing a set of local minima and local maxima of the baseline PPG signal, and processing the set of local minima and local maxima to obtain a set of processed local minima and local maxima values. An upper threshold value and a lower threshold value may be set based on the set of processed local minima and local maxima values; and one or more regions of the baseline PPG signal may be selected by selecting regions for which signal amplitude values of the baseline PPG signal are located within the lower threshold value and the upper threshold value. In an embodiment, the upper threshold value and lower threshold value may be set to a multiple of the median value of the local maxima and a multiple of the median value of the local minima, respectively.

In an embodiment, a filter transformation may correspond to a low-pass filter operation or a wavelet transformation. In an embodiment, a portion of the original PPG signal may be processed based on the up strokes and down strokes of the original PPG signal. In an embodiment, the signal parameter for extraction may be the respiration rate of a patient.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
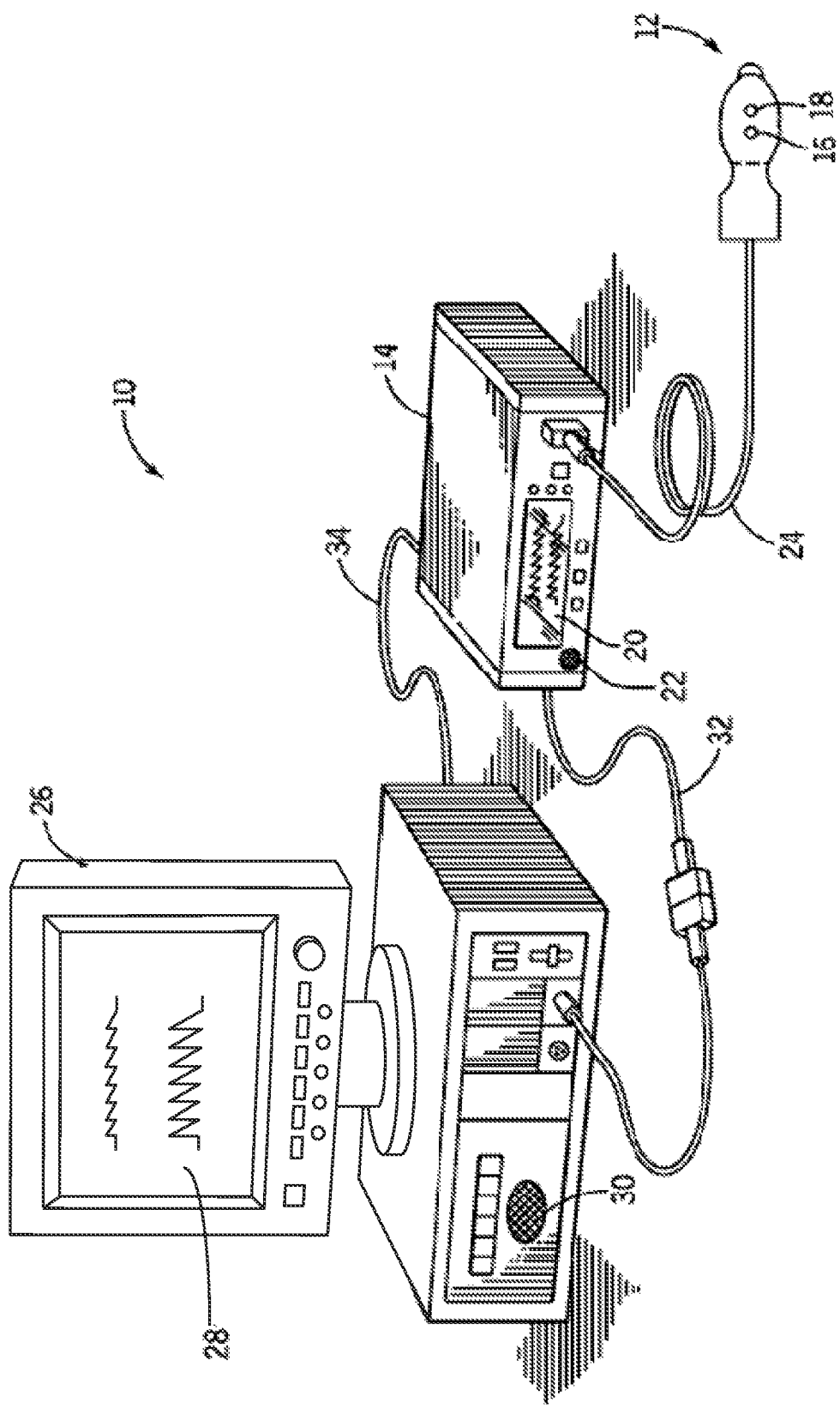
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o, \beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.
1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R)+(1-s)\beta_r(\lambda_R)}{s\beta_o(\lambda_{IR})+(1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR})-\beta_r(\lambda_{IR})) - \frac{d\log I(\lambda_{IR})}{dt}(\beta_o(\lambda_R)-\beta_r(\lambda_R))}$$

Note in discrete time $$\frac{d\log I(\lambda,t)}{dt} \simeq \log I(\lambda, t_2) - \log I(\lambda, t_1)$$

Using log A-log B=log A/B, $$\frac{d\log I(\lambda, t)}{dt} \simeq \log\left(\frac{I(t_2,\lambda)}{I(t_1,\lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1,\lambda_R)}{I(t_2,\lambda)}\right)}{\log\left(\frac{I(t_1,\lambda_{IR})}{I(t_2,\lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR})-\beta_r(\lambda_{IR})) - \beta_o(\lambda_R)+\beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2,\lambda_R)-I(t_1,\lambda_R)}{I(t_1,\lambda_R)}}{\frac{I(t_2,\lambda_{IR})-I(t_1,\lambda_{IR})}{I(t_1,\lambda_{IR})}} \quad (7)$$

$$= \frac{[I(t_2,\lambda_R)-I(t_1,\lambda_R)]I(t_1,\lambda_{IR})}{[I(t_2,\lambda_{IR})-I(t_1,\lambda_{IR})]I(t_1,\lambda_R)}$$

$$= R$$

which defines a cluster of points whose slope of y versus x will give R where $$x(t) = [I(t_2, \lambda_{IR}) - I(t_1, \lambda_{IR})] I(t_1, \lambda_R)$$

$$y(t) = [I(t_2, \lambda_{IR}) - I(t_1, \lambda_{IR})] I(t_1, \lambda_{IR})$$

$$y(t) = Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
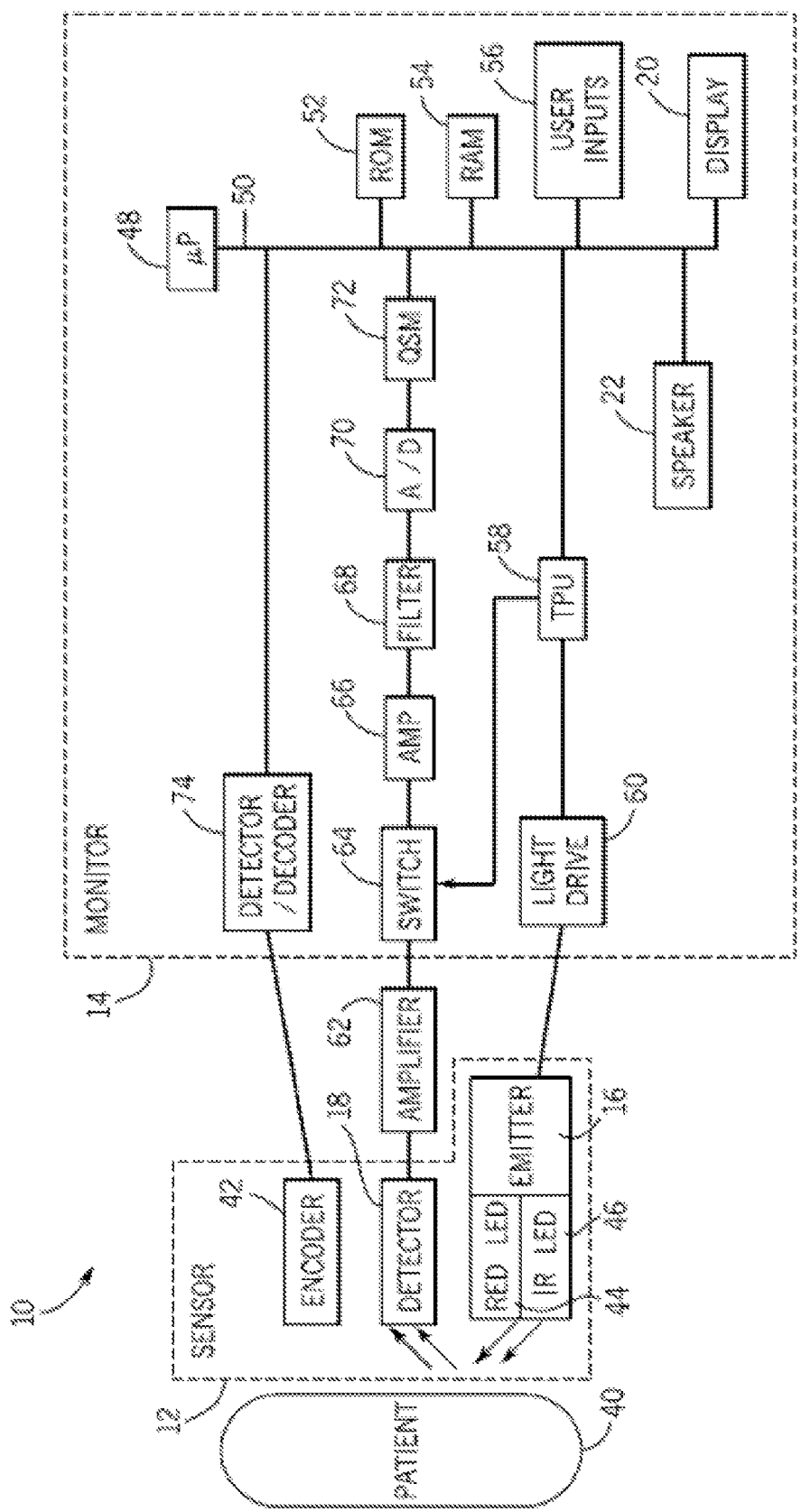
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signal and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \qquad (9)$$

where ψ*(t) is the complex conjugate of the wavelet function ψ(t), a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \qquad (10)$$

where '|' is the modulus operator. The scalogram may be rescaled for useful purposes. One common rescaling is defined as $$S_R(a, b) = \frac{|T(a, b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unsealed wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
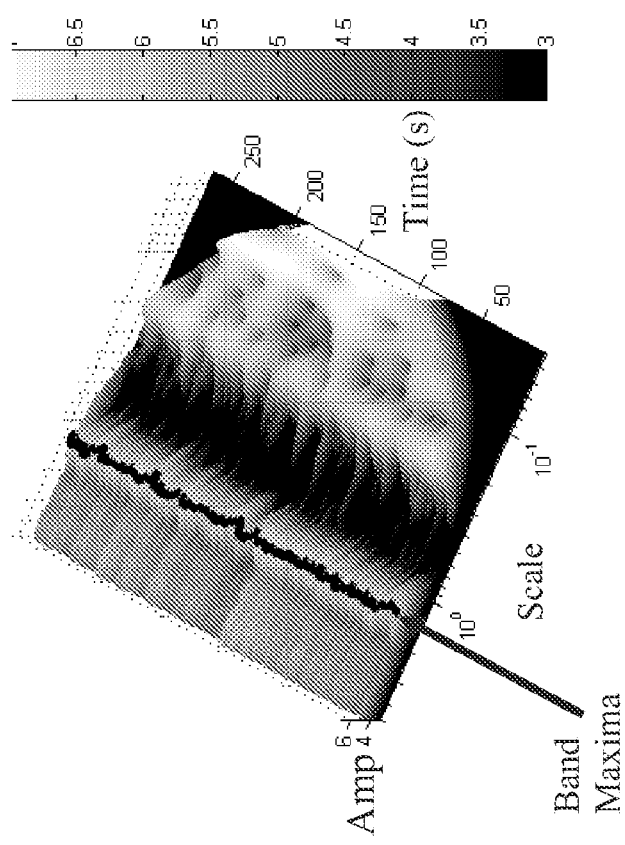
FIGS. 3(a) and 3(b) show illustrative views of a scalogram derived from a PPG signal in accordance with an embodiment.
Figure 3A:
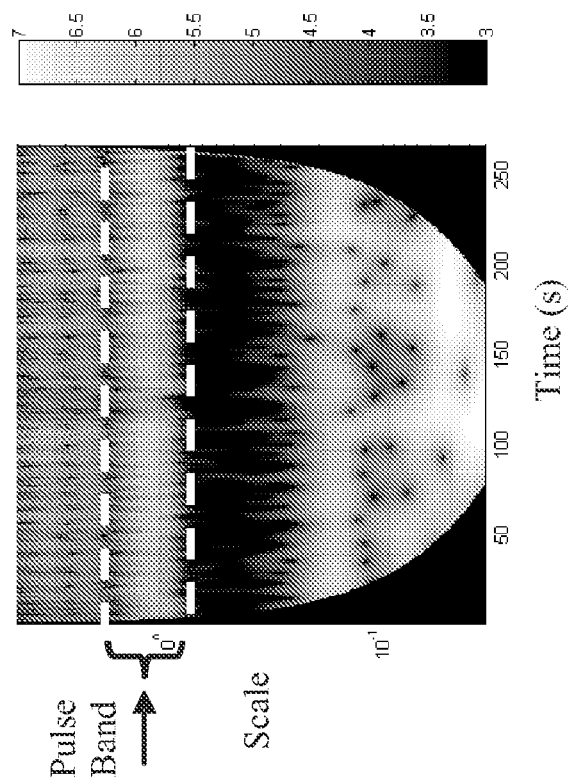

Pertinent repeating features in a signal give rise to a time-scale band in wavelet space or a resealed wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
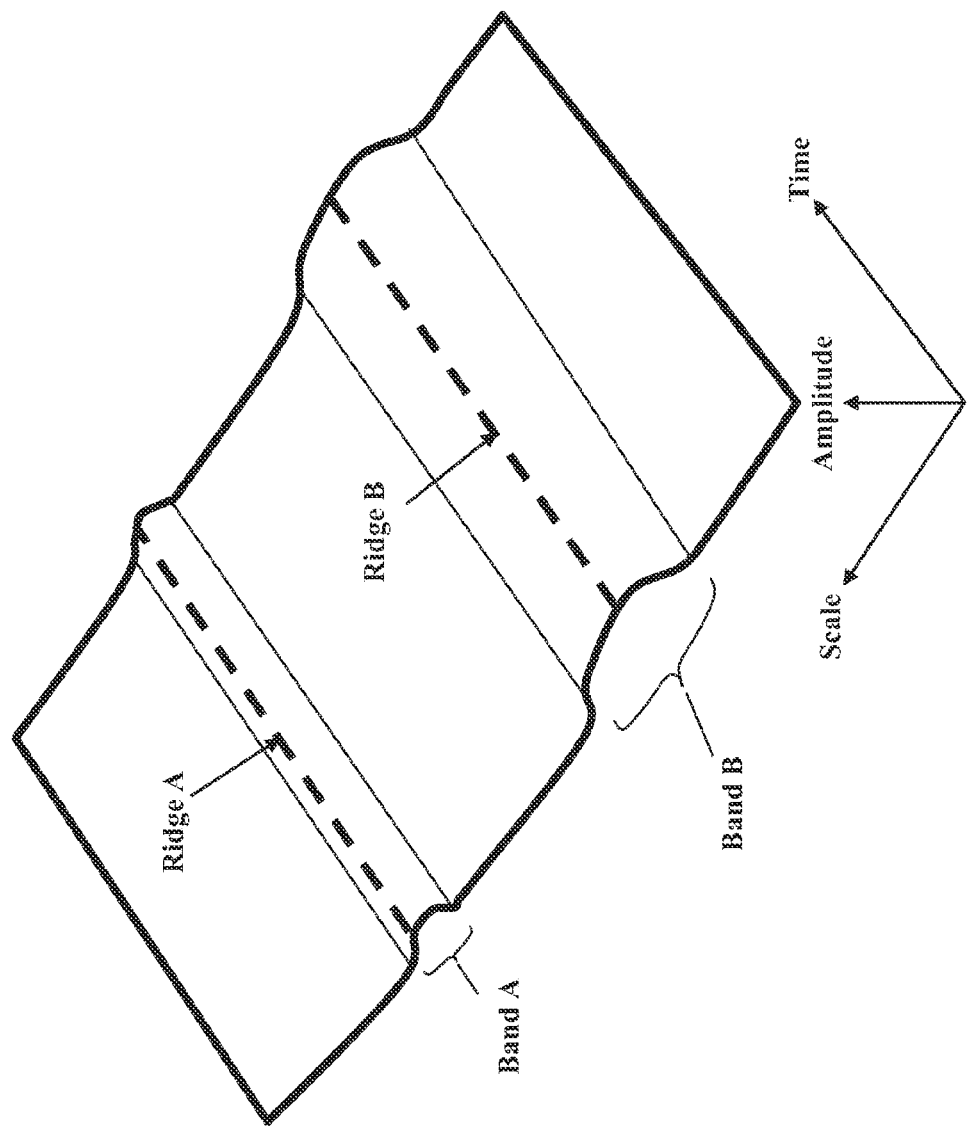
FIG. 3(c) shows an illustrative scalogram derived from a signal containing two pertinent components in accordance with an embodiment.
Figure 3D:
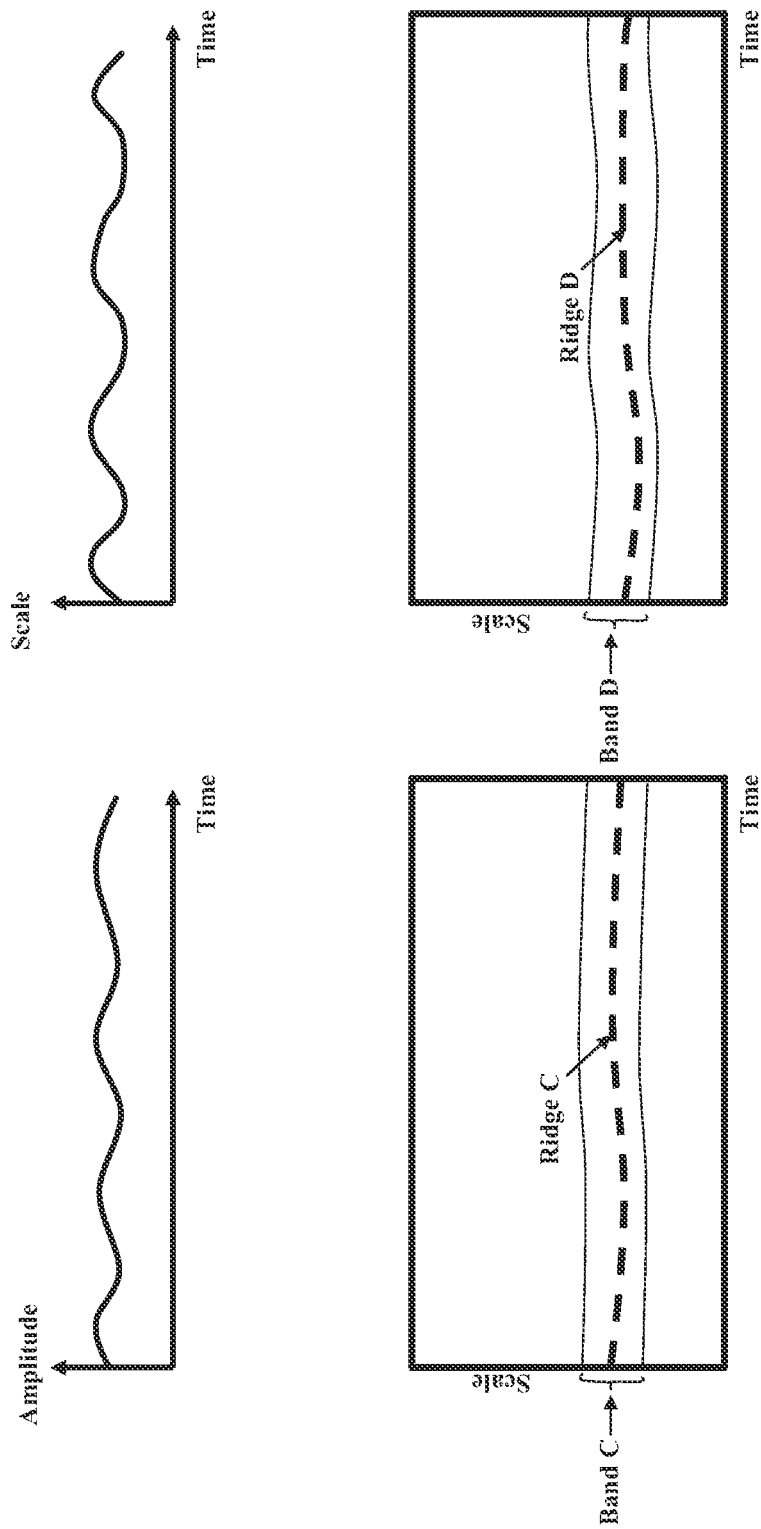
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \qquad (15)$$

which may also be written as:

$$x(t) = \frac{1}{C_g} \int_{-\infty}^{\infty} \int_0^{\infty} T(a,b) \psi_{a,b}(t) \frac{da\,db}{a^2} \qquad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \qquad (17)$$

Figure 3E:
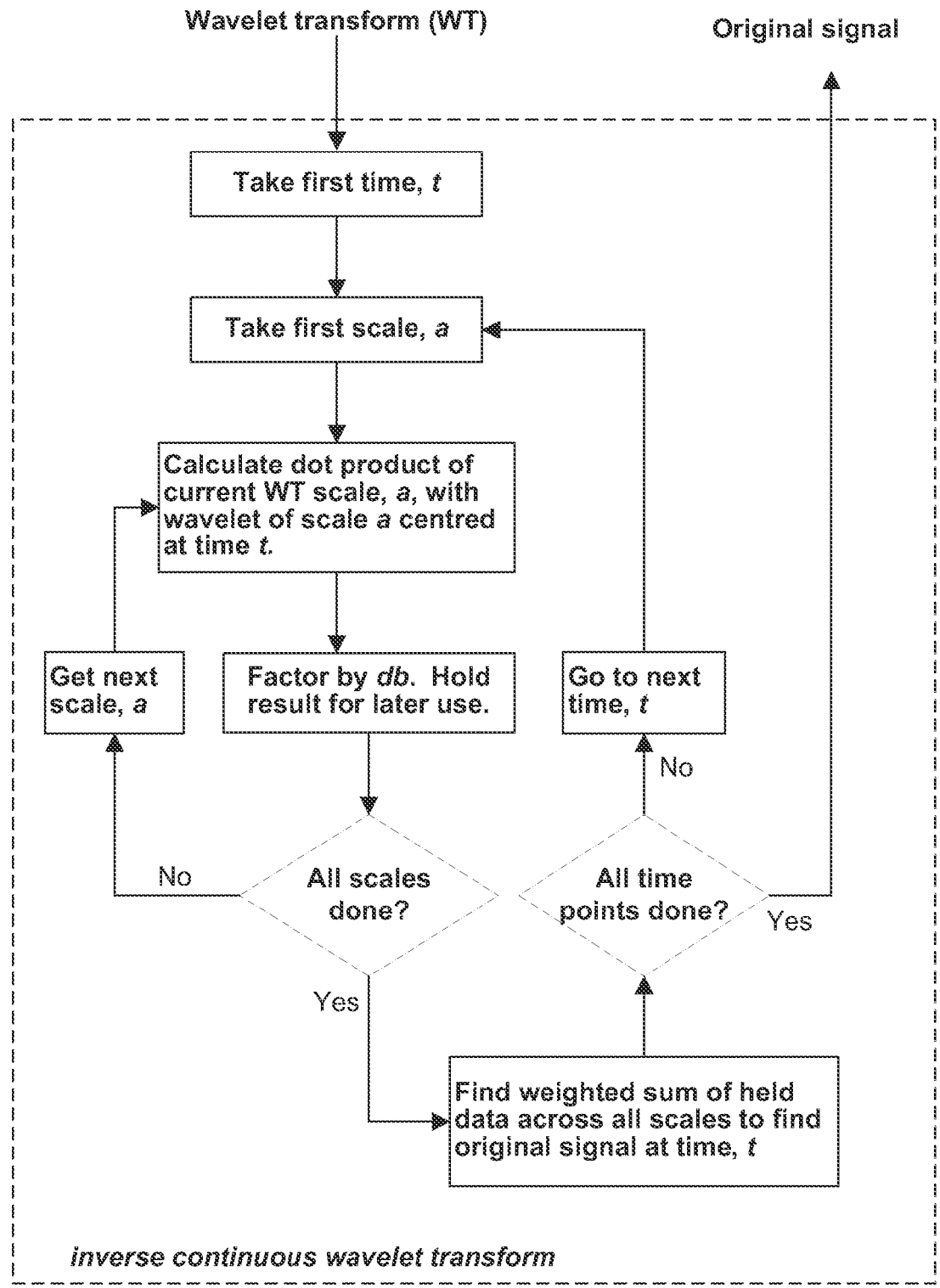
FIGS. 3(e) and 3(f) are flow charts of illustrative steps involved in performing an inverse continuous wavelet transform in accordance with embodiments.
Figure 3F:
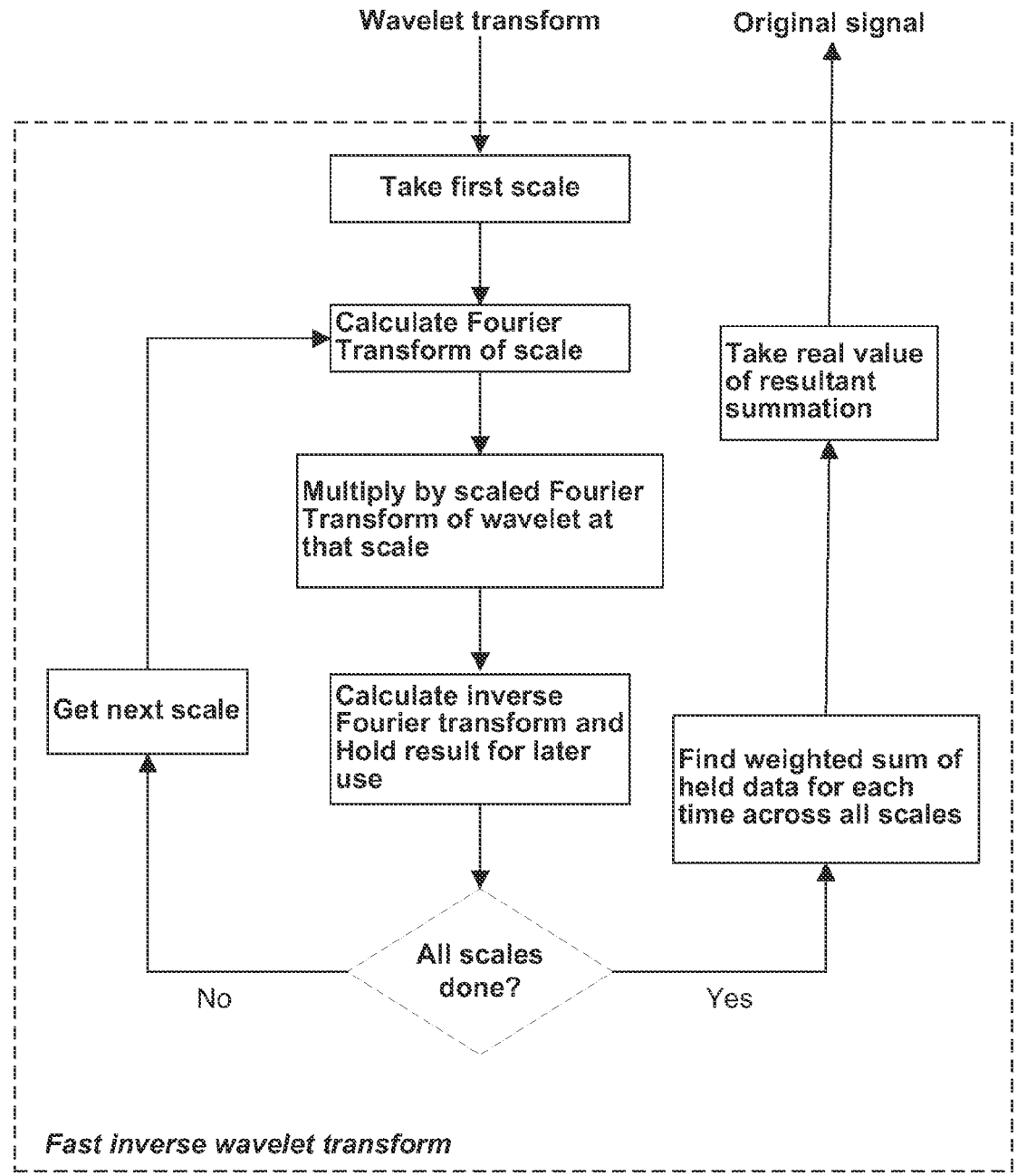

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
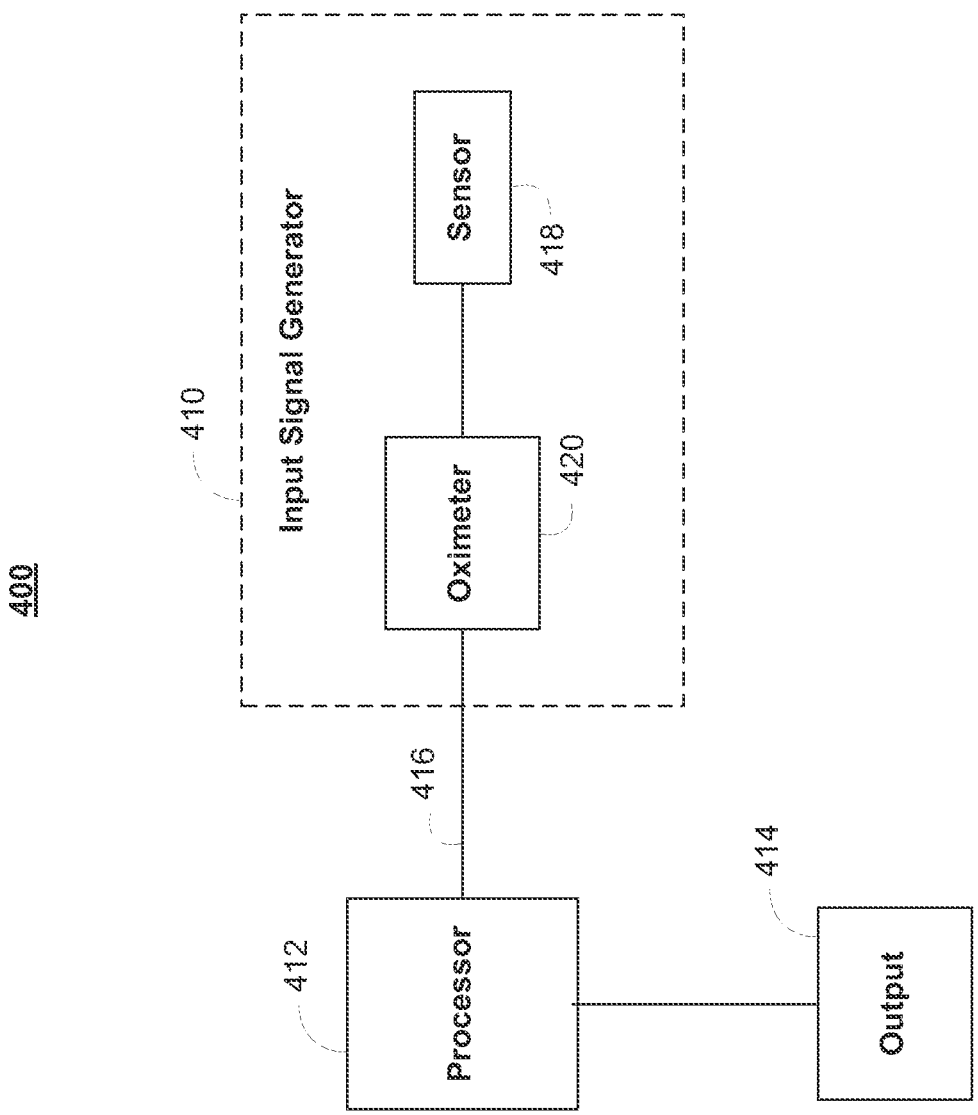
FIG. 4 is a block diagram of an illustrative continuous wavelet processing system in accordance with some embodiments.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Figure 5:
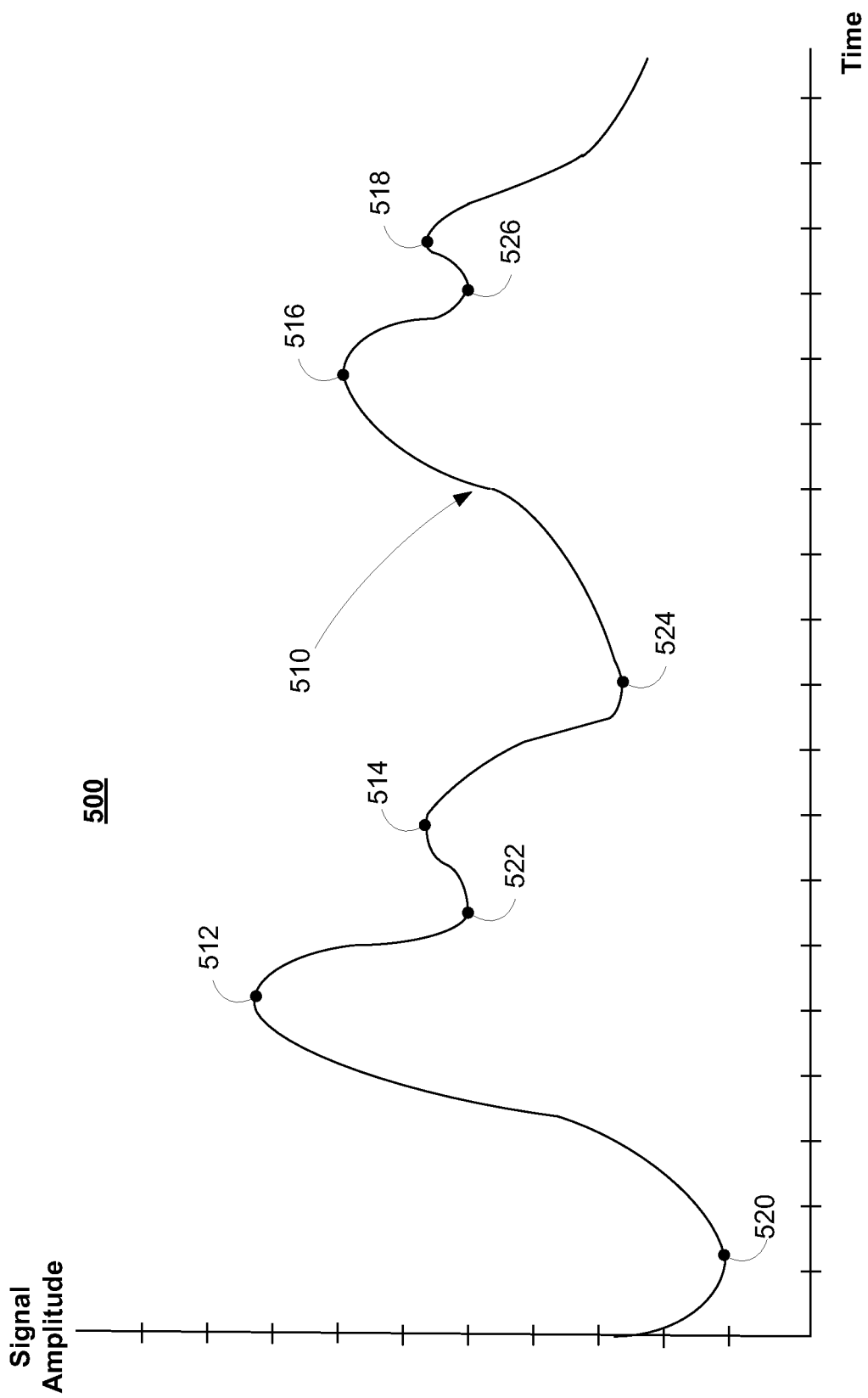
FIG. 5 is an illustrative plot of a PPG signal that may obtained from a pulse oximetry system, e.g., the pulse oximetry system of FIG. 1 in accordance with an embodiment.

FIG. 5 is an illustrative plot of a PPG signal that may obtained from a pulse oximetry system, such as pulse oximetry system 10 (FIG. 1). Plot 500 displays time on the x-axis and signal amplitude values (of PPG signal 510) on the y-axis. PPG signal 510 may be obtained from a patient, such as patient 40 (FIG. 2), and may be obtained using a sensor such as sensor 12 (FIG. 1). Alternatively, PPG signal 510 may be obtained by averaging or otherwise combining multiple signals derived from a suitable sensor array, as discussed in relation to FIG. 1. Plot 500 may be displayed using any suitable display device such as, for example, display 20 or 28 (both of FIG. 1), a PDA, a mobile device, or any other suitable display device. Additionally, plot 500 may be displayed on multiple display devices.

PPG signal 510 may exhibit an oscillatory behavior versus time, and may include several undulations of varying signal amplitude level and frequency. For example, the undulations of PPG signal 510 may be partially or fully characterized by signal minima and signal maxima, such as signal maxima 512, 514, 516, and 518 and/or signal minima 520, 522, 524, and 526. The size, shape, and/or frequency of the undulations of PPG signal 510 may be indicative of an underlying parameter, e.g., a biological parameter, of a patient from which the PPG signal is obtained. In an embodiment, PPG signal 510 may measure the breathing cycle of a patient such as patient 40 (FIG. 2), and PPG signal 510 may be processed to extract the respiration rate of the patient.

PPG signal 510 may contain erroneous or otherwise undesirable artifacts due to, for example, patient movement, equipment failure, and/or various noise sources. For example, cable 24, cable 32, and/or cable 34 (all of FIG. 1) may malfunction or become loosened from the equipment to which it is connected. Further, sensor 12 (FIG. 1), or any constituent component of sensor 12 (FIG. 1) (for example, emitter 16 (FIG. 1) and/or detector 18 (FIG. 1)) may malfunction and/or become loosened. Additionally, noise sources may produce undesired artifacts in PPG signal 510. Possible sources of noise include thermal noise, shot noise, flicker noise, burst noise, and/or electrical noise caused by light pollution. These and other noise sources may be introduced, for example, through sensor 12 (FIG. 1), and/or cables 24, 32, and 34 (all of FIG. 1) These and/or other undesirable artifacts may be present in PPG signal 510 and may have an adverse effect on the extraction of a biosignal parameter (or any other type of suitable parameter) from PPG signal 510. For example, undesired artifacts present in PPG signal 510 may reduce the accuracy of extraction, and increase the amount of signal data and acquisition-time required to extract a biosignal parameter from PPG signal 510.

Therefore, it may be advantageous to select a suitable region of a biosignal, e.g. PPG signal 510, prior to parameter extraction, at least to minimize the number or amount of undesirable artifacts present in the selected region. Performing parameter extraction on a suitable region of a biosignal, rather than on the entire biosignal, may increase the precision and reliability of the extraction and/or decrease the acquisition time and computational resources required to perform the extraction. Further, a suitable region of the biosignal, e.g. PPG signal 510, may be selected to include relatively low noise and or be time-invariant with respect to the value of the underlying parameter, e.g., a patient respiration rate. The selected suitable region may exhibit statistical regularity and/or other features that match closely or identically the features used to derive parameter extraction algorithms. Therefore, such algorithms may exhibit relatively strong performance, e.g., detection or estimation performance, when applied to a suitable region of a biosignal such as PPG signal 510. Process 600 (FIG. 6) depicts an illustrative process that may be used to extract a biosignal parameter from a suitable region of the biosignal in accordance with an embodiment.

Although the techniques disclosed herein are described mostly in the context of selecting a suitable region of a PPG signal, e.g., PPG signal 510, for the determination of respiration information (e.g., the respiration rate of a patient), the disclosed techniques may be applied to any other suitable signal and/or parameter. For example, the disclosed techniques may be applied to any generally repetitive signal, and the use of a PPG signal to illustrate the disclosed techniques is for clarity of presentation only. For example, the disclosed techniques may be applied signals such as transthoracic impedance signals, and/or capnograph signals, in addition to non-biological signals. PPG signal 510 or any other suitable signal may be obtained from a source other than pulse oximeter system 10 (FIG. 1). For example, PPG signal 510 may be obtained from another type of medical device or from non-medical devices such as a general signal oscilloscope and/or waveform analyzer. Further, the techniques disclosed herein may be applied to signals that, e.g., have more or less frequent undulations than PPG signal 510, time-variant mean amplitude values, noise patterns, and/or discontinuities. The techniques described herein may be applied to PPG signals that do not resemble the time-varying pattern of PPG signal 510 shown in FIG. 5. For example, PPG signal 510 may be a simplified illustration of a PPG signal measured in practice.

Figure 6:
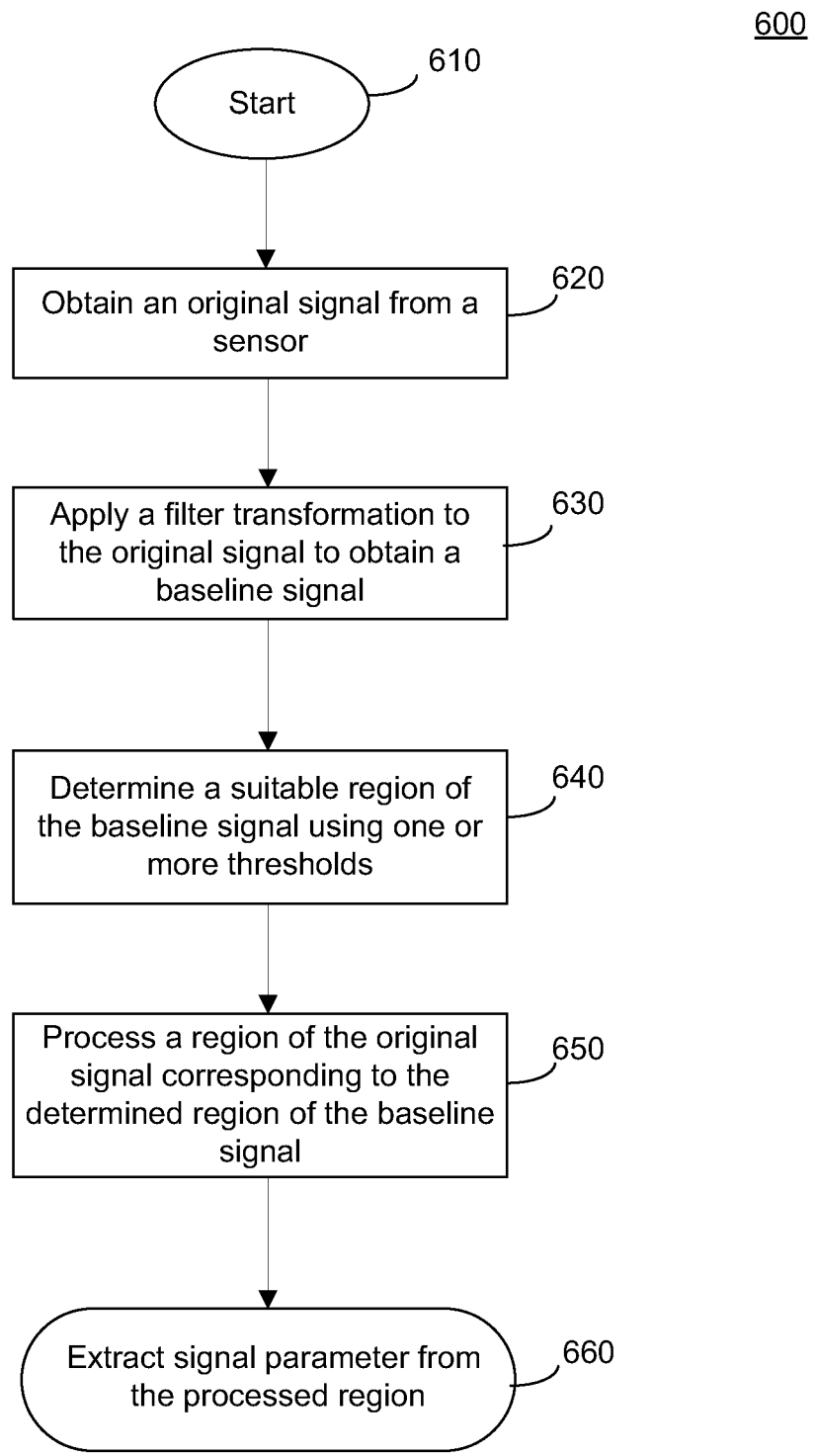
FIG. 6 depicts an illustrative process that may be used to extract a parameter from a processed region of a signal, e.g., a PPG signal, in accordance with an embodiment.

FIG. 6 depicts an illustrative process that may be used to select a suitable region of a biosignal, and extract a biosignal parameter from the suitable region, in accordance with an embodiment. Although process 600 describes extraction of a biosignal parameter from a biosignal for clarity of presentation, process 600 may be used to extract any suitable signal parameter from any generally repetitive signal.

Process 600 may start at step 610. At step 620, process 600 may obtain signal, which will be referred to as the original PPG signal. The original PPG signal may be a PPG signal such as PPG signal 510 (FIG. 5) or any other suitable biosignal or generally repetitive (possibly non-biological) signal. The original PPG signal may be obtained using a sensor such as sensor 12 (FIG. 1) to measure biological characteristics of a patient such as patient 40 (FIG. 2). Additionally, the original PPG signal may obtained in real-time or it may be a signal previously obtained and stored in memory, for example, ROM 52 (FIG. 2) or RAM 54 (FIG. 2). The original PPG signal obtained at step 620 may be obtained by first obtaining a preliminary PPG signal and processing the preliminary PPG signal. The preliminary PPG signal may be obtained using, e.g., sensor 12 (FIG. 1) and processed using a processor such as processor 412 (FIG. 4) or microprocessor 48 (FIG. 2) in a system similar or identical to pulse oximetry system 10 (FIG. 1).

At step 630, a filter transformation may be applied to the original PPG signal, e.g., PPG signal 510 (FIG. 5) to obtain a baseline signal. The filter transform applied at step 630 may be used to partially or fully isolate non-signal and/or noise artifacts present in the original PPG signal for further analysis, and may be performed, for example, by processor 412 (FIG. 2) or microprocessor 48 (FIG. 2). For example, process 600 may apply a low-pass filter at step 630 to exclude the frequency content of the original PPG signal that is over a certain threshold frequency value. The filter may be an analog or digital filter applied, e.g., by circuitry including pulse oximetry monitor 14 (FIG. 1), and various parameters of the filter, including the cutoff frequency may be adjusted by a user using user inputs 56 (FIG. 2). The threshold value may depend on known characteristics of the desired signal component present in the original PPG signal, and various threshold values may be stored, e.g., in ROM 52 (FIG. 2) or RAM 54 (FIG. 2). For example, if the original PPG signal obtained at step 620 is a noisy signal representing patient respiration, then a low-pass filter may be applied at step 630 that excludes signal frequencies above, e.g., 0.7 Hz (other frequency cutoff values may also be used as appropriate, e.g., based on known characteristics of the signal component present in the original PPG signal). In an embodiment, the baseline signal represents the original PPG signal obtained at step 610 with the pulse component of the signal partially or fully removed. The baseline signal may include only lower-frequency signal components. Illustrative baseline signals obtained by applying a filter transformation to an original PPG signal, e g. the original PPG signal of FIG. 5, are illustrated in plot 700 (FIG. 7) and plot 800 (FIG. 8).

In addition or alternatively to a low-pass filter, process 600 may apply a wavelet filter transform and/or other wavelet methods at step 630 to the signal obtained at step 610. Wavelet methods applied at step 630 may be advantageous, e.g., in representing the original PPG signal obtained at step 620 in a time and scale representation. The pulse component of the original PPG signal may then be removed using detection and estimation and/or other signal processing techniques.

Figure 9A:
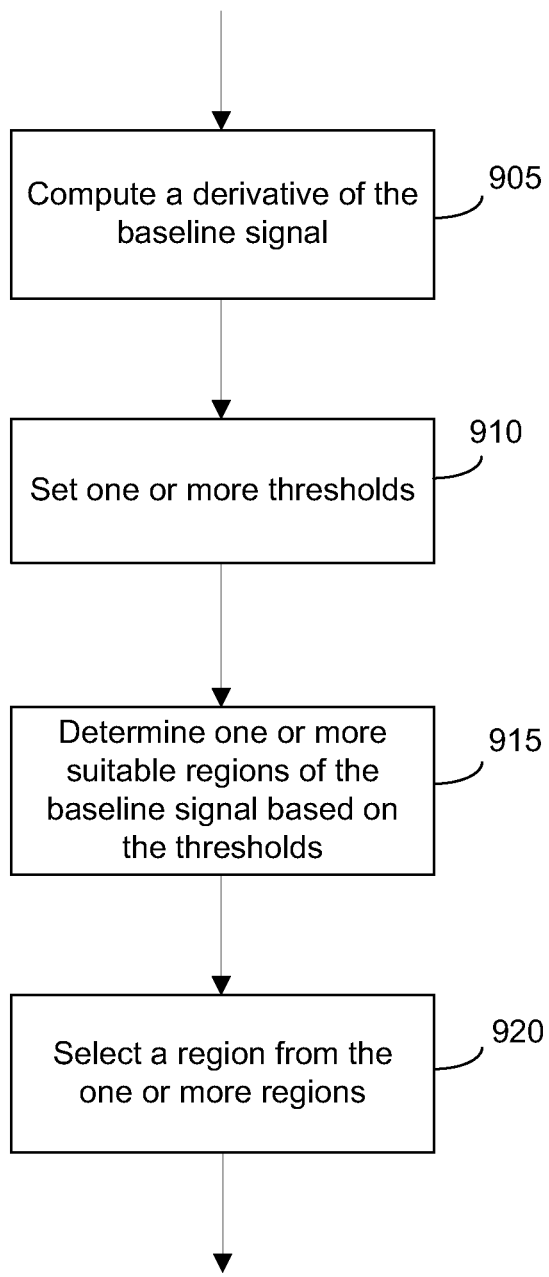
FIG. 9A depicts an illustrative process for determining a suitable region of a baseline signal by processing the derivative of amplitude values of the signal in accordance with an embodiment.
Figure 9B:
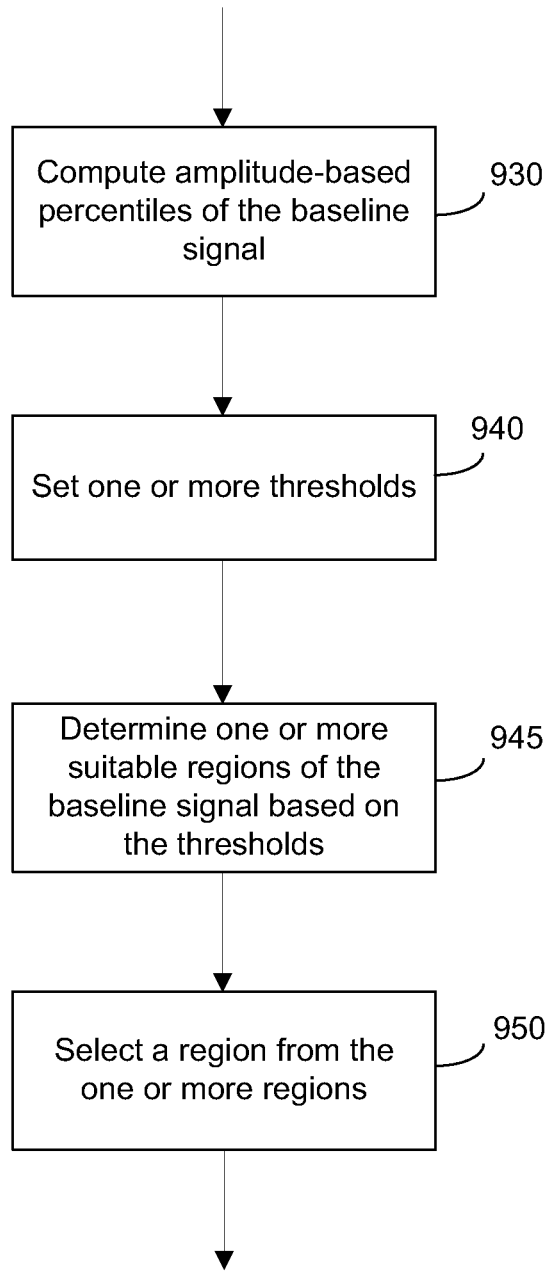
FIG. 9B depicts an illustrative process for determining a suitable region of a baseline signal by processing the percentile-exceeding amplitude values of the signal in accordance with an embodiment.
Figure 9C:
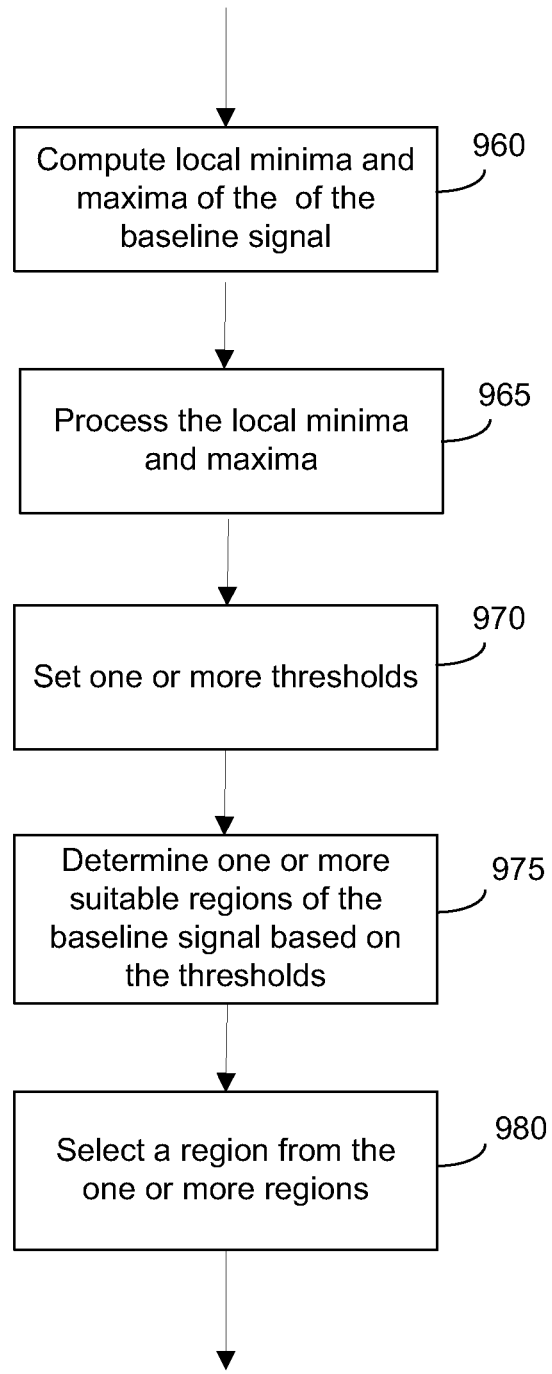
FIG. 9C depicts an illustrative process for determining a suitable region of a baseline signal by processing the local minima and maxima of the signal in accordance with an embodiment.

At step 640, process 600 may determine a suitable region of the baseline signal that may be used for further analysis and extraction of, e.g., a biosignal parameter. Process 600 may use any suitable method to determine a suitable region of the baseline signal. For example, process 600 may identify "non-analyzable" regions of the baseline signal (and hence, identify suitable regions of the baseline signal) by identifying regions of the baseline signal that exceed or fall below preset thresholds. The thresholds used by process 600 may be set, e.g., by an operator using user inputs 56 (FIG. 2), and calculations related to setting the thresholds may be performed by processor 412 (FIG. 2) and/or microprocessor 48 (FIG. 2) and stored in ROM 52 (FIG. 2) and/or RAM 54 (FIG. 2). Thresholds used by process 600 may be determined according to any number of criteria. In an embodiment, thresholds used by process 600 at step 640 to identify a suitable region of the baseline signal may be set, e.g., as a multiple of the standard deviation of the signal over an analysis window. In an embodiment thresholds used by process 600 at step 640 to identify a suitable region of the baseline signal may be set by processing the derivative of amplitude values of the signal, as illustrated in process 900 (FIG. 9A). In an embodiment, thresholds used by process 600 at step 640 to identify a suitable region of the baseline signal may be set by processing the percentile-exceeding amplitude values of the signal, as illustrated in process 925 (FIG. 9B). In an embodiment, thresholds used by process 600 at step 640 to identify a suitable region of the baseline signal may be set by processing the local minima and maxima of the signal, as illustrated in process 955 (FIG. 9C).

At step 650, process 600 may process a region of the original PPG signal corresponding to the region of the baseline signal identified at step 640. For example, if the analysis at step 640 reveals that the baseline signal has a suitable region for analysis in a given time window, e.g., the time window consisting of times from 0 to 20, then the original PPG signal may be processed within this time window to remove undesired artifacts and other non-signal components from the original PPG signal obtained at step 620 of process 600. For example, process 600 may detect and process the up and down strokes of the region of the baseline signal identified at step 640 using techniques similar or identical to those described in Watson, U.S. Provisional Application No. 61/077,092, filed Jun. 30, 2008, entitled "Systems and Method for Detecting Pulses," which is incorporated by reference herein in its entirety. In an embodiment, a portion of the region of the baseline signal identified at step 640 may be selected and minored to reduce undesirable artifacts caused by the non-selected portion of the preliminary PPG signal. In an embodiment, the region of the baseline signal identified at step 640 may be selected and mirrored at step 650. In an embodiment, Secondary Wavelet Feature Decoupling (SWFD) may be used on the region of the baseline signal identified at step 640. In an embodiment, sub-regions of the region of the baseline signal identified at step 640 may be selected and concatenated using techniques similar or identical to those described in McGonigle et al., U.S. Application Ser. No. 12/437,317, filed May 7, 2009, entitled "Concatenated Scalograms Produced By Signal Processing Mirroring Technique," which is incorporated by reference herein in its entirety.

At step 660, the processed region determined at step 650 may be used to extract a signal parameter. For example, the processed region may be used to determine the occurrence of certain features, such as a respiration rate of a patient (e.g., patient 40 (FIG. 2)). One embodiment of step 660 is illustrated by process 1000 (FIG. 10), where a patient respiration rate may be extracted and reported.

Figure 7:
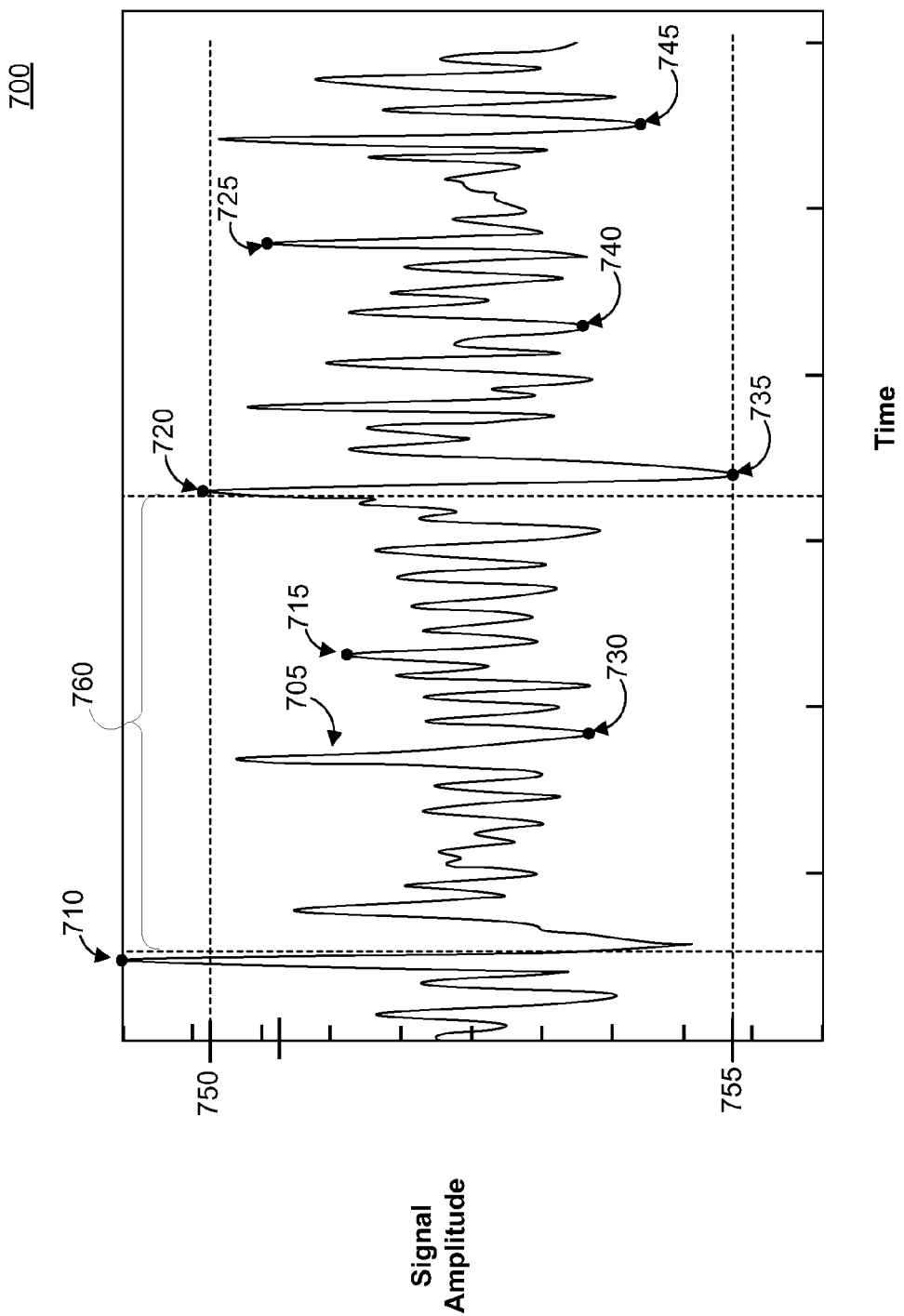
FIGS. 7 and 8 depict baseline signals that may be obtained by applying a filter transformation to an original PPG signal, e.g. the PPG signal of FIG. 5, in accordance with an embodiment.
Figure 8:
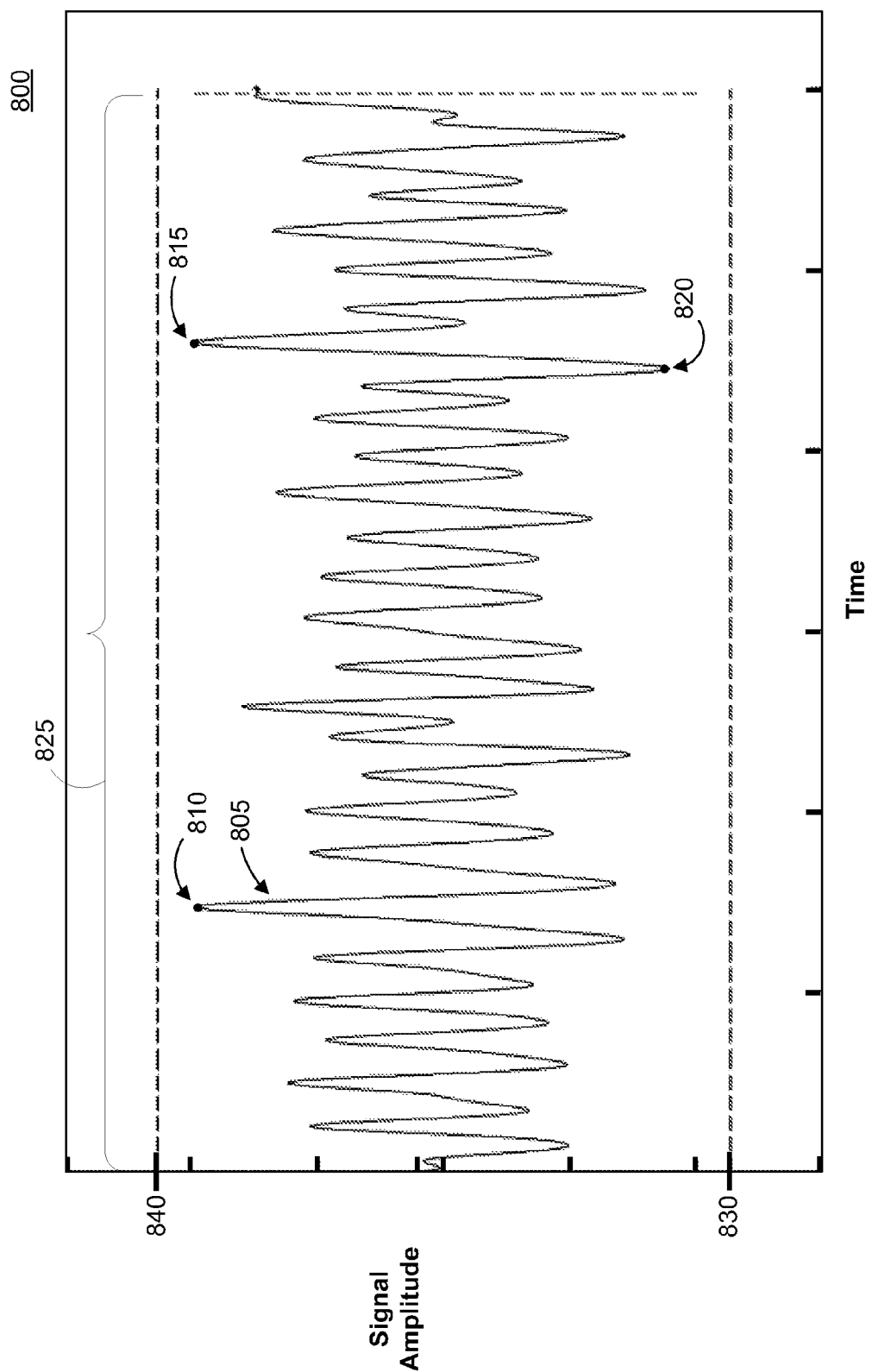

FIG. 7 depicts a baseline signal that may be obtained by applying a filter transformation to an original PPG signal in accordance with an embodiment. For example, baseline signal 705 may be obtained by first obtaining an original PPG signal at step 620 of process 600 (both of FIG. 6), e.g. PPG signal 510 (FIG. 5), and then applying a low-pass filter to the original PPG signal at step 630 of process 600 (FIG. 6).

Baseline signal 705 may reflect the original PPG signal obtained at step 620 (FIG. 6) with a pulse or signal component of the original PPG signal partially or fully removed, and baseline signal 705 may therefore partially reflect the residual undesired artifacts present the original PPG signal. The filtered PPG may now be inspected to find regions which are analyzable. In some embodiments, this may include most parts except for a few excursions. Baseline signal 705 may be displayed using display 20 or 28 (both of FIG. 1), and may exhibit an oscillatory behavior versus time, and may include several undulations of varying signal amplitude level and frequency. For example, pulse oximetry system 10 (FIG. 1) may characterize the undulations of baseline signal 705 by identifying and/or storing the values of signal maxima and signal minima, such as signal maxima 710, 715, 720, and 725 and signal minima 730, 735, 740, and 745. The size, shape, and/or frequency of the undulations of baseline signal 705 may indicate the time-regions of the original PPG signal that have the most noise and/or undesired artifacts. For example, in plot 700 it may be determined (e.g., by an operator using user inputs 56 (FIG. 2) to analyze baseline signal 705) that a certain region of baseline signal 705 (e.g. region 760) reflects a consistent and stable region of the corresponding original PPG signal. This region may be selected as a suitable region for analysis to obtain a physiological parameter of interest, e.g. a patient respiration rate. For example, region 760 may be selected as an analyzable region of the original PPG signal obtained at step 620 of process 600, as region 760 is bounded by two high-amplitude signal regions (i.e., the high-amplitude region having a right-boundary at signal maximum 710 and the high-amplitude region having a left-boundary at signal maximum 720) which exceed the upper threshold 750. Generally, the regions of baseline signal 705 that lie above an upper threshold or below a lower threshold may be marked as non-analyzable (or "unsuitable") regions. For example, in FIG. 7, the region having a right-boundary at signal maximum 710 and the region having a left-boundary at signal maximum 720 exceed upper threshold 750. Such non-analyzable regions may be relatively short in time-duration, as depicted in FIG. 7, or they may be longer in duration, depending on the underlying noise and/or artifacts.

Upper threshold 750 and/or lower threshold 755 may be used to isolate time-regions of baseline signal 705 that are non-analyzable (and therefore, may be used to identify a suitable region of the baseline signal). For example, upper threshold 750 and/or lower threshold 755 may be set to identify a suitable region of baseline signal 705 by processing derivative values of baseline signal 705, as illustrated in process 900 (FIG. 9A), identifying percentile-exceeding amplitude values of baseline signal 705, as illustrated in process 925 (FIG. 9B), and/or characterizing local minima and maxima of baseline signal 705, as illustrated in process 955 (FIG. 9C). The values of upper threshold 750 and/or lower threshold 755 may be displayed on a display, for example, display 20 or 28 (both of FIG. 1), and may be controlled by user inputs 56 (FIG. 2). Additionally, more or fewer thresholds may be used and/or controlled by user inputs 56 (FIG. 2).

The thresholds may also be set by software running on a processor such as processor 412 (FIG. 2) and/or microprocessor 48 (FIG. 2), and predetermined values for the thresholds may be stored, e.g., in ROM 52 (FIG. 2) and/or RAM 54 (FIG. 2).

FIG. 8 depicts another baseline signal that may be obtained by applying a filter transformation to an original PPG signal in accordance with an embodiment. Baseline signal 805 may reflect the original PPG signal obtained at step 620 (FIG. 6) with a pulse or signal component of the original PPG signal partially or fully removed, and baseline signal 805 may therefore partially reflect residual and/or undesired artifacts present the original PPG signal. Baseline signal 805 may be displayed using display 20 or 28 (both of FIG. 1), and may exhibit an oscillatory behavior versus time. For example, baseline signal 805 may include several undulations of varying signal amplitude level and frequency. Baseline signal 805 may be partially or fully characterized by signal minima and signal maxima, such as signal maxima 810 and 815 and/or signal minimum 820. The size, shape, and/or frequency of the undulations of baseline signal 805 may indicate the time-regions of the original PPG signal that have the most noise and/or undesired artifacts. For example, in plot 800, pulse oximetry system 10 (FIG. 1) may set and/or utilize lower threshold 830 and upper threshold 840 to determine a suitable region of baseline signal 805, e.g., at step 640 of process 600 (both of FIG. 6). A suitable region of baseline signal 805 may be set and/or determined by using processor 412 (FIG. 2) or microprocessor 48 (FIG. 2) in parallel with user inputs 56 (FIG. 2), and may be determined to be a region of baseline signal 805 for which all signal points are located within amplitude values bounded by lower threshold 830 and upper threshold 840. FIG. 8 depicts that baseline signal 805 is relatively consistent over the entire analysis window (e.g., no amplitude value in baseline signal 805 is larger than upper threshold 840 or smaller than lower threshold 830). In this case, the entire signal, denoted by region 825, may be selected as a suitable region, e.g., at step 640 of process 600 (both of FIG. 6).

FIG. 9A depicts an illustrative process that a pulse oximetry system, e.g., pulse oximetry system 10 (FIG. 1), may use to determine a suitable region of a baseline signal, e.g., baseline signal 705 (FIG. 7) or 805 (FIG. 8), in accordance with an embodiment. Process 900 may be implemented using processor 412 (FIG. 2) and/or microprocessor 48 (FIG. 2). Process 900 may determine the derivative of amplitude values of the baseline signal in accordance with an embodiment. Process 900 may be a further embodiment of step 640 of process 600 (both of FIG. 6). For example, process 900 may set and/or adjust one or more threshold values related to the derivate of amplitude values of baseline signal 705 (FIG. 7) or 805 (FIG. 8).

At step 905, process 900 may compute a derivative of a baseline signal, e.g., the baseline signal obtained at step 630 of process 600 (FIG. 6). For example, Process 900 may compute the derivate, or any suitable approximation thereof, using analytic methods, numerical analysis, or a combination of these and any other techniques. In an embodiment, process 900 may compute the derivative of a baseline signal by first using linear or high-order curve fitting techniques to determine an analytic representation for the baseline signal, e.g., baseline signal 705 (FIG. 7) or 805 (FIG. 8), and then using numerical or analytic methods to compute the derivative of the baseline signal based on the analytic representation. In an embodiment, process 900 may compute the derivate, or a suitable approximation of the derivative, using numerical differentiation techniques, for example, based on a method of difference quotients. Process 900 may compute the derivative of the baseline signal by performing computations using processor 412 (FIG. 2) or microprocessor 48 (FIG. 2), and storing the results in, e.g., in ROM 52 (FIG. 2) or RAM 54 (FIG. 2). Additionally, calculations or graphics related to a computation of the derivative may be displayed on display 20 or 28 (both of FIG. 1), and parameters used to calculate the derivative, e.g., tolerance and initial point values, may be adjusting using user inputs 56 (FIG. 2).

The magnitude of the derivative values (or gradient values) determined at step 905 may indicate a region of significant artifacts and/or noise in the baseline signal. At step 910, process 900 may set one or more thresholds, e.g., using processor 412 (FIG. 2) or microprocessor 48 (FIG. 2) based on the derivative values computed at step 905. The one or more thresholds may be set based, e.g., on prior knowledge that derivative values exceeding a certain threshold value indicate a non-analyzable region of a signal. For example, the derivate of baseline signal 705 (FIG. 7) may be computed at step 905, and an upper threshold may be set at a numerical value of 10 (or any other suitable numerical value, e.g., stored in ROM 52 (FIG. 2) and/or RAM 54 (FIG. 2)) at step 910.

At step 915, one or more suitable regions of the baseline signal may be determined based on the thresholds set at step 910. For example, regions of the derivate of the baseline signal having values exceeding this threshold value may be marked (or otherwise interpreted) as non-analyzable sections of the baseline signal, while regions having values equal to and/or below the threshold may be marked as analyzable regions of the signal. For example, the derivative of baseline signal 705 (FIG. 7) may be computed at step 905, and it may be determined that region 760 (FIG. 7) consists of derivative values all of which are below the set threshold, while the derivative values outside of region 760 (FIG. 7) all exceed the set threshold. In this case, region 760 may be selected as a suitable region of baseline signal 705 (FIG. 7). Additionally or alternatively, a minimum threshold value may be set at step 910, and any regions of the baseline signal having derivative values below this lower threshold value may be marked by, e.g., pulse oximetry system 10, as non-analyzable regions of the baseline signal. In this way, one or more suitable regions of a baseline signal, e.g., baseline signal 705 (FIG. 7) or 805 (FIG. 8) may be determined based on the upper and/or lower thresholds set at step 910.

At step 920, process 900 may select a region from the one or more suitable regions determined at step 915. For example, the selected region may be the region having the longest time-duration of the regions determined at step 915 or it may be the first occurring suitable region in time. Alternatively, the region selected at step 920 may be selected by an operator using user inputs 56 (FIG. 2), and/or the selected region may be the only suitable region determined at step 915.

FIG. 9B depicts an illustrative process that a pulse oximetry system, e.g., pulse oximetry system 10 (FIG. 1), may use to determine a suitable region of a baseline signal, e.g., baseline signal 705 (FIG. 7) or 805 (FIG. 8), in accordance with an embodiment. Process 925 may be implemented using processor 412 (FIG. 2) and/or microprocessor 48 (FIG. 2). Process 925 may determine the percentile-exceeding amplitude values of the baseline signal in accordance with an embodiment. Process 925 may be a further embodiment of step 640 of process 600 (both of FIG. 6). For example, process 900 may set and/or adjust one or more threshold values related to the percentile-exceeding amplitude values of baseline signal 705 (FIG. 7) or 805 (FIG. 8).

At step 930, process 925 may compute amplitude-based percentiles of a baseline signal, e.g., the baseline signal obtained at step 630 of process 600 (FIG. 6). To do so, process 925 may first compute or tabulate signal amplitude values of the baseline signal, e.g., baseline signal 705 (FIG. 7) or 805 (FIG. 8), using any suitable technique, such as discrete signal sampling. In an embodiment, process 925 may store data on the amplitudes of the baseline signal in ROM 52 (FIG. 2) and/or RAM 54 (FIG. 2), and may process and analyze percentile data using processor 412 (FIG. 2) or microprocessor 48 (FIG. 2). At step 930, process 925, may map percentile values of the baseline signal to corresponding amplitude values of the baseline signal. For example, process 925 may store the time-locations of a baseline signal which exceed the 95th-percentile of the amplitude values (and/or any other suitable percentage) at step 930. Process 925 may store such values in, e.g., ROM 52 (FIG. 2) or RAM 54 (FIG. 2).

At step 940, process 900 may set a threshold, e.g. upper threshold 750 (FIG. 7) when operating on baseline signal 705 (FIG. 7), so that a percentage of the baseline signal (corresponding to one of the percentile values determined at step 930) lies below the threshold. For example, process 900 may set upper threshold 750 (FIG. 7) so that upper threshold 750 (FIG. 7) is greater than 95-percent of the amplitude values of baseline signal 700 (FIG. 7). Similarly, more than one threshold value may be set at step 940 based on the computations conducted and stored at step 930. For example, process 900 may set lower threshold 755 (FIG. 7) to one-percent (i.e., one-percent of the amplitude values of baseline signal 705 (FIG. 7) lie below lower threshold 755 (FIG. 7)).

Alternatively, process 900 may set thresholds based on a suitable multiple of a percentile. For example, process 900 may operate on baseline signal 805 (FIG. 8), and may set upper threshold 840 to be twice (i.e., a factor of two) larger in value than the 95th-percentile of amplitude values of the baseline signal 805 (FIG. 8). Similarly, process 900 may set lower threshold 830 (FIG. 8) to a value one-third the value of the 30th-percentile of amplitude values of baseline signal 805 (FIG. 8). Further, any other suitable multiplicative factors and/or percentile values may be used by process 900 at step 940. Setting threshold values at step 940 may be accomplished using, e.g., processor 412 (FIG. 2) or microprocessor 48 (FIG. 2), and/or may be partially or fully controlled by an operator using user inputs 56 (FIG. 2) and a visual display of the signal, e.g., shown on display 20 or 28 (both of FIG. 1).

At step 945, one or more suitable regions of the baseline signal e.g., baseline signal 705 (FIG. 7) or 805 (FIG. 8), may be determined based on the thresholds set at step 940. For example, regions the of the baseline signal having values exceeding an upper threshold, e.g., upper threshold 750 of FIG. 7, or below a lower threshold value, e.g., lower threshold 755 of FIG. 7, may be marked (or otherwise interpreted) as non-analyzable sections of the baseline signal. In an embodiment, lower threshold 755 and upper threshold 750 (both of FIG. 7) may be set relative to the mean amplitude value of the corresponding baseline signal, i.e., baseline signal 705 (FIG. 7). The mean amplitude value may be determined and/or stored, e.g., at step 930. Similarly, regions having values equal to and/or below the threshold may be marked as analyzable regions of the signal. In an embodiment, signal regions between regions where the baseline signal has exceed at least one of the thresholds set at step 940 are marked as regions suitable for analysis. For example, at step 945, it may be determined at region 760 (FIG. 7) is a suitable region of baseline signal 705 (FIG. 7), as the amplitude values of baseline signal 705 (FIG. 7) lie fully within lower threshold 755 (FIG. 7) and upper threshold 750 (FIG. 7). In this way, one or more suitable regions of a baseline signal, e.g., baseline signal 705 (FIG. 7) may be determined based on the thresholds set at step 940.

At step 950, process 900 may select a region from the one or more suitable regions determined at step 945. For example, the selected region may be the region having the longest time-duration of the regions determined at step 945 or it may be the first occurring suitable region in time. The time and/or amplitude values corresponding to the selected region may be stored in memory, e.g., in ROM 52 (FIG. 2) or RAM 54 (FIG. 2), and may be selected using, e.g., processor 412 (FIG. 2) or microprocessor 48 (FIG. 2). Alternatively, the region selected at step 950 may be selected by an operator using user inputs 56 (FIG. 2), and/or the selected region may be the only suitable region determined at step 945.

FIG. 9C depicts an illustrative process that a pulse oximetry system, e.g., pulse oximetry system 10 (FIG. 1), may use to determine a suitable region of a baseline signal, e.g., baseline signal 705 (FIG. 7) or 805 (FIG. 8), in accordance with an embodiment. Process 955 may be implemented using processor 412 (FIG. 2) and/or microprocessor 48 (FIG. 2). Process 955 may determine some of all of the local minima and maxima of the baseline signal in accordance with an embodiment. Process 955 may be a further embodiment of step 640 of process 600 (both of FIG. 6). For example, process 955 may set and/or adjust one or more threshold values related to some or all of the local minima and maxima of baseline signal 705 (FIG. 7) or 805 (FIG. 8).

At step 960, process 955 may identify and/or compute local minima and maxima of a baseline signal, e.g., the baseline signal obtained at step 630 of process 600 (FIG. 6). For example, baseline signal 705 may be obtained at step 630 of process 600 (both of FIG. 6), and signal maxima 710, 715, 720, and 725 and/or signal minima 730, 735, 740, and 745 may be computed at step 960 of process 955. Process 955 may compute and/or identify signal minima and maxima using a suitable signal processing algorithm, such as an extrema-finding algorithm performed by processor 412 (FIG. 2) or microprocessor 48 (FIG. 2). Further process 955 may store the time-locations and values of signal minima and maximum, e.g., in ROM 52 (FIG. 2) or RAM 54 (FIG. 2).

At step 965, process 955 may process or otherwise transform the signal minima and maxima identified and/or stored at step 960. For example, process 955 may compute a median value of signal minima and/or a median value of signal maxima, and may store these values, e.g., in ROM 52 (FIG. 2) or RAM 54 (FIG. 2). Additionally or alternatively, process 955 may compute a multiple of one or both of these values and store these results in memory, such as ROM 52 (FIG. 2) or RAM 54 (FIG. 2). Further, the particular values used in computations at step 965 may be determined by an operator who views candidate minima and maxima on a display, such as display 20 or 28 (both of FIG. 1) and selects minima and/or maxima using user inputs 56 (FIG. 2).

At step 970, process 900 may set one or more thresholds based, e.g., on the minima and/or maxima (and any related transformation) computed and stored at step 965. For example, process 955 may set upper threshold 750 (FIG. 7) to be the median or mean value of the signal maxima computed at step 965, and may set lower threshold 755 (FIG. 7) to be the median or mean value of the signal minima computed at step 960 and/or 965. Process 955 may set thresholds based on a suitable multiple of any of the values computed at step 965. For example, process 955 may operate on baseline signal 805 (FIG. 8), and set upper threshold 840 to be twice (i.e., a factor of two) larger in value than the median of the maxima of the baseline signal 805 (FIG. 8) (e.g., the median of signal maxima such as signal maxima 810 and 815 of FIG. 8). Similarly, process 955 may set lower threshold 830 (FIG. 8) to the median of the minima of the baseline signal 805 (FIG. 8) (e.g., the median of signal minima such as signal minima 820 of FIG. 8). Further, any other suitable multiplicative factors and/or threshold values may be used by process 955 at step 970. Setting threshold values at step 970 may be accomplished using, e.g., processor 412 (FIG. 2) or microprocessor 48 (FIG. 2), and/or may be partially or fully controlled by an operator using user inputs 56 (FIG. 2) and a visual display of the signal, e.g., shown on display 20 or 28 (both of FIG. 1).

At step 975, one or more suitable regions of the baseline signal e.g., baseline signal 705 (FIG. 7) or 805 (FIG. 8), may be determined based on the thresholds set at step 970. For example, regions of the baseline signal having values exceeding an upper threshold, e.g., upper threshold 750 of FIG. 7, or below a lower threshold value, e.g., lower threshold 755 of FIG. 7, may be marked (or otherwise interpreted) as non-analyzable sections of the baseline signal. In an embodiment, regions having values equal to and/or below the threshold may be marked as analyzable regions of the signal. In an embodiment, signal regions between regions where the baseline signal has exceed at least one of the thresholds set at step 970 are marked as regions suitable for analysis. For example, at step 975, it may be determined at region 760 (FIG. 7) is a suitable region of baseline signal 705 (FIG. 7), as the amplitude values of baseline signal 705 (FIG. 7) lie fully within lower threshold 755 (FIG. 7) and upper threshold 750 (FIG. 7). In this way, one or more suitable regions of a baseline signal, e.g., baseline signal 705 (FIG. 7) may be determined based on the thresholds set at step 970.

At step 980, process 955 may select a region from the one or more suitable regions determined at step 975. For example, the selected region may be the region having the longest time-duration of the regions determined at step 975 or it may be the first occurring suitable region in time. The time and/or amplitude values corresponding to the selected region may be stored in memory, e.g., in ROM 52 (FIG. 2) or RAM 54 (FIG. 2), and may be selected using, e.g., processor 412 (FIG. 2) or microprocessor 48 (FIG. 2). Alternatively, the region selected at step 980 may be selected by an operator using user inputs 56 (FIG. 2), and/or the selected region may be the only suitable region determined at step 975.

Figure 10:
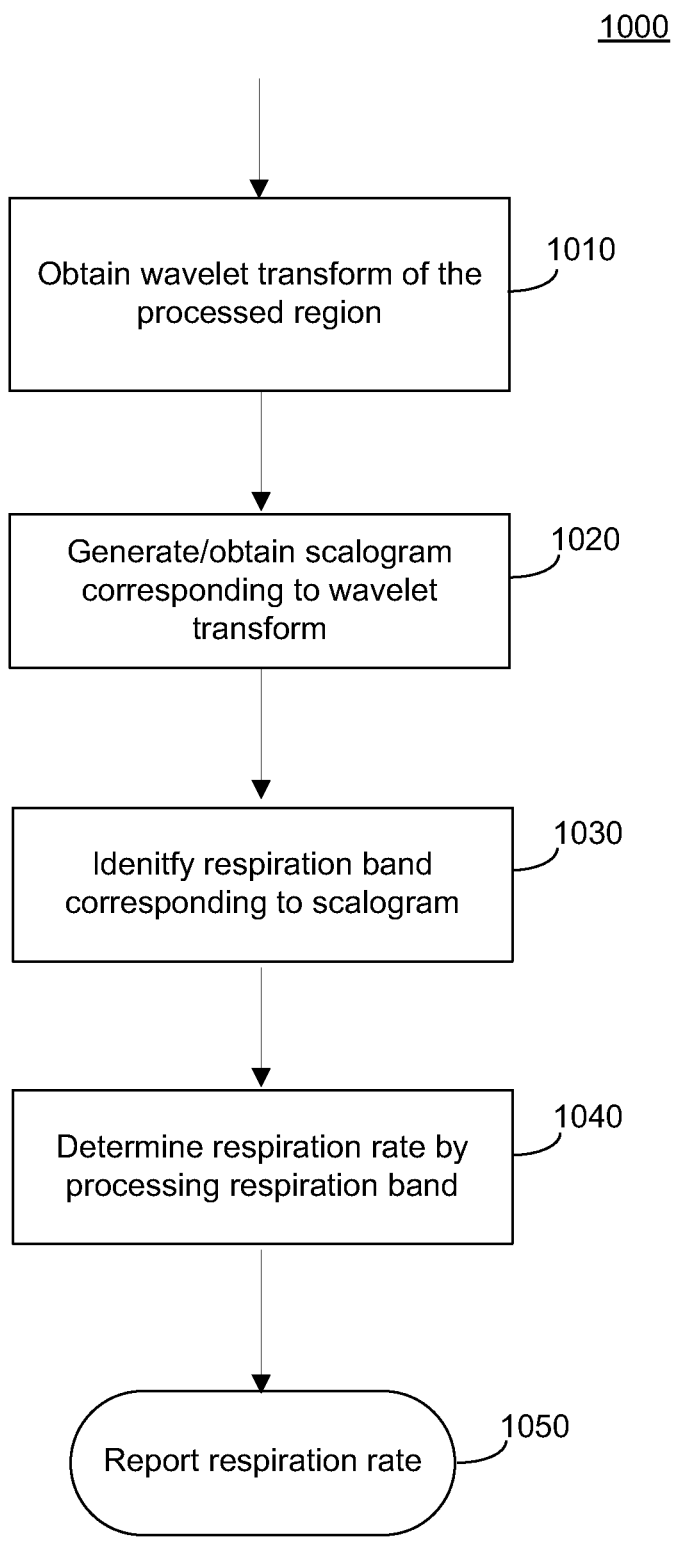
FIG. 10 depicts an illustrative process for extracting a signal parameter from a processed region of a signal, e.g. a PPG baseline signal, in accordance with an embodiment.

FIG. 10 depicts an illustrative process that may be used by pulse oximetry system 10 (FIG. 1) to extract a signal parameter from a processed region of a signal, e.g. a PPG baseline signal, in accordance with an embodiment. Process 1000 may correspond to a further embodiment of step 660 of process 600. Process 1000 may be used by pulse oximetry monitor 14 (FIG. 1) to extract (e.g., estimate and/or detect) the respiration rate of patient, such as patient 40 (FIG. 2), from a processed region of a baseline signal, e.g., as described at step 650 of FIG. 6 and in FIGS. 9A-9C.

At step 1010, the wavelet transform of a processed region of a baseline signal, e.g., a processed region of baseline signal 705 (FIG. 7) or 805 (FIG. 8) may be obtained. A wavelet transform may be obtained, for example, by system 10 (FIGS. 1 and 2) or system 400 (FIG. 4). At step 1020, the scalogram of the wavelet transform may be generated or otherwise obtained using, for example a processor such as processor 412 (FIG. 4) or microprocessor 48 (FIG. 2). In addition to the scalogram, other parts of the wavelet transform may be determined at step 1020. For example, the transform modulus, phase, real, and/or imaginary parts may be generated at step 1020 in addition to the scalogram. Each of these features may then be used, either individually or in combination, in the subsequent steps of process 1000 to extract the respiration rate of a patient.

At step 1030, the respiration band of a scalogram may identified based on one or more characteristics of the scalogram obtained in step 1020. The respiration band of the scalogram may generally reflect the breathing pattern of a patient, e.g., patient 40 (FIG. 2). The respiration band of the scalogram obtained in step 1020 may be identified using characteristics of the scalogram such as the energy and structure of the scalogram, and the signal-to-noise levels in various regions of scalogram. In one embodiment, this information may be calculated one or more times using different time-window sizes. The number and type of time-window sizes that are used may depend on the anticipated respiration rate, the available computational resources (e.g., the amount of ROM 52 (FIG. 2) and/or RAM 54 (FIG. 2) and the speed of processor 412 (FIG. 4) and/or microprocessor 48 (FIG. 2)), as well as on possible input derived from user inputs 56 (FIG. 2).

At step 1040, the scalogram characteristics determined in step 1030 corresponding to the respiration band may be analyzed. Analyzing the characteristics may generally involve parsing, combining, and/or weighing results obtained in previous steps of process 1000 to obtain a single, overall estimate of the respiration rate. Step 1040 may incorporate the use of past scalogram data that has been obtained in previous iterations of process 1000 to extract a respiration rate. The respiration rate may be represented, e.g., by a digital or analog number from 1 to 100, where a larger number indicates a larger respiration rate (any other suitable continuous or non-continuous number range may be used instead). Step 1040 may also involve the parameterization and/or curve fitting of data obtained in steps 1020 and 1030 using, for example, linear least-squares fitting of the data or any other suitable interpolation technique. The disclosed parameterization and/or curve fitting may be performed, for example, by processor 412 (FIG. 4) or microprocessor 48 (FIG. 2), and may additionally depend on parameters entered by a user through user inputs 56 (FIG. 2). To extract a respiration rate at step 1040, process 1000 may use, for example, maximum-likelihood detection techniques to combine data when the prior probability of a given respiration rate is known, and/or Neyman-Pearson combining techniques when the prior probability of a given respiration rate is unknown.

At step 1050, the respiration rate determined or estimated at step 1040 may be reported. For example, the respiration rate may be reported by generating an audible alert or, for example, using speaker 22 (FIG. 2) as well as possibly through other audio devices, generating an on-screen message, for example, on display 20 (FIG. 1) or display 28 (FIG. 1), generating a pager message, a text message, or a telephone call, for example, using a wireless connection embedded or attached to a system such as system 10 (FIG. 1), activating a secondary or backup sensor or sensor array, for example, connected through a wire or wirelessly to monitor 14 (FIG. 1), or regulating the automatic administration medicine, for example, which is controlled in part or fully through a system such as system 10 (FIG. 1).

It will also be understood that the above method may be implemented using any human-readable or machine-readable instructions on any suitable system or apparatus, such as those described herein.

The foregoing is merely illustrative of the principles of this disclosure and various modifications may be made by those skilled in the art without departing from the scope and spirit of the disclosure. The following claims may also describe various aspects of this disclosure.

What is claimed is:

1. A method of extracting a signal parameter from a generally repetitive signal, comprising:
   obtaining, using a specifically programmed processor, an original photoplethysmograph (PPG) signal from a sensor;
   applying, using the specifically programmed processor, a filter transformation to the original PPG signal to substantially remove a pulse component from the original PPG signal and produce a baseline PPG signal;
   determining, using the specifically programmed processor, one or more regions of the baseline PPG signal by applying a threshold to the baseline PPG signal, wherein the values of the threshold depend, at least in part, on a set of signal amplitude values of the baseline PPG signal;
   selecting, using the specifically programmed processor, a region from the one or more regions, and processing a portion of the original PPG signal corresponding to the selected region; and
   extracting, using the specifically programmed processor, the signal parameter from the processed portion of the original PPG signal.

2. The method of claim 1, wherein the determining one or more regions of the baseline PPG signal further comprises:
   computing, processor, a set of derivative values of the baseline PPG signal;
   setting, using the specifically programmed processor, an upper threshold value and a lower threshold value based on the computed set of derivative values; and
   determining, using the specifically programmed processor, one or more regions of the baseline PPG signal by selecting regions of the baseline PPG signal having derivative values located within the lower threshold value and the upper threshold value.

3. The method of claim 1, wherein the determining one or more regions of the baseline PPG signal further comprises:
   computing, processor, a set of amplitude-based percentile values of the baseline PPG signal;
   setting, using the specifically programmed processor, an upper threshold value and a lower threshold value based on the computed set of amplitude-based percentile values; and
   determining, using the specifically programmed processor, one or more regions of the baseline PPG signal by selecting regions of the baseline PPG signal having amplitude-based percentile values located within the lower threshold value and the upper threshold value.

4. The method of claim 1, wherein the determining one or more regions of the baseline PPG signal further comprises:
   computing, using the specifically programmed processor, a set of local minima and local maxima of the baseline PPG signal;
   processing, using the specifically programmed processor, the set of local minima and local maxima to obtain a set of processed local minima and local maxima values;
   setting, using the specifically programmed processor, an upper threshold value and a lower threshold value based on the obtained set of processed local minima and local maxima values; and
   determining, using the specifically programmed processor, one or more regions of the baseline PPG signal by selecting regions of the baseline PPG signal having processed local minima and local maxima values located within the lower threshold value and the upper threshold value.

5. The method of claim 1, wherein applying the filter transformation comprises applying a low-pass filter.

6. The method of claim 1, wherein applying the filter transformation comprises applying a wavelet transformation.

7. The method of claim 1, wherein processing the portion of the original PPG signal comprises detecting and transforming up strokes and down strokes of the original PPG signal.

8. The method of claim 1, wherein the extracted signal parameter comprises an estimated value of a respiration rate of a patient.

9. The method of claim 1, wherein a first threshold is set to a value that is a first multiple of the standard deviation of the amplitude values of the baseline PPG signal, and a second threshold is set to a value that is a second multiple of the standard deviation of the amplitude values of the baseline PPG signal.

10. The method of claim 4, wherein the upper threshold is set to a value that is a multiple of the median value of the local maxima, and the lower threshold is set to a value that is a multiple of the median value of the local minima.

11. A system for extracting a signal parameter from a generally repetitive signal, comprising:
    a sensor for obtaining an original photoplethysmograph (PPG) signal;
    a processor coupled to the sensor, wherein the processor is configured to:
      apply a filter transformation to the original PPG signal to substantially remove a pulse component from the original PPG signal to produce a baseline PPG signal;
      determine one or more regions of the baseline PPG signal by applying a threshold to the baseline PPG signal, wherein the values of the threshold depend, at least in part, on a set of signal amplitude values of the baseline PPG signal;
      select a region from the determined one or more regions;
      process a portion of the original PPG signal corresponding to the selected region; and
      extract the signal parameter from the processed portion of the original PPG signal.

12. The system of claim 11, wherein the processor is further configured to determine one or more regions of the baseline PPG signal by:
    computing a set of derivative values of the baseline PPG signal;
    setting an upper threshold value and a lower threshold value based on the computed set of derivative values; and
    determining one or more regions of the baseline PPG signal by selecting regions of the baseline PPG signal having derivative values located within the lower threshold value and the upper threshold value.

13. The system of claim 11, wherein the processor is further configured to determine one or more regions of the baseline PPG signal by:
    computing a set of amplitude-based percentile values of the baseline PPG signal;
    setting an upper threshold value and a lower threshold value based on the computed set of amplitude-based percentile values; and
    determining one or more regions of the baseline PPG signal by selecting regions of the baseline PPG signal having amplitude-based percentile values located within the lower threshold value and the upper threshold value.

14. The system of claim 11, wherein the processor is further configured to determine one or more regions of the baseline PPG signal by:
    computing a set of local minima and local maxima of the baseline PPG signal;

processing the set of local minima and local maxima to obtain a set of processed local minima and local maxima values;

setting an upper threshold value and a lower threshold value based on the obtained set of processed local minima and local maxima values; and determining one or more regions of the baseline PPG signal by selecting regions of the baseline PPG signal having processed local minima and local maxima values located within the lower threshold value and the upper threshold value.

15. The system of claim 11, wherein the processor is further configured to apply the filter transformation, at least in part, by applying a low-pass filter.

16. The system of claim 11, wherein the processor is further configured to apply the filter transformation, at least in part, by applying a wavelet transformation.

17. The system of claim 11, wherein the processor is further configured to process the portion of the original PPG signal by detecting and transforming up strokes and down strokes of the original PPG signal.

18. The system of claim 11, wherein the extracted signal parameter comprises an estimated value of a respiration rate of a patient.

19. The system of claim 11, wherein the processor is further configured to set a first threshold value that is a first multiple of the standard deviation of the amplitude values of the baseline PPG signal, and a set a second threshold value that is a second multiple of the standard deviation of the amplitude values of the baseline PPG signal.

20. The system of claim 14, wherein the processor is further configured to set the upper threshold to a value that is a multiple of the median value of the local maxima, and set the lower threshold to a value that is a multiple of the median value of the local minima.

* * * * *